US010842833B2

(12) United States Patent
Kim et al.

(10) Patent No.: US 10,842,833 B2
(45) Date of Patent: *Nov. 24, 2020

(54) LACTOBACILLUS PLANTARUM AND COMPOSITION COMPRISING SAME

(71) Applicant: CJ CHEILJEDANG CORP, Seoul (KR)

(72) Inventors: Bong Joon Kim, Inchon (KR); Heon Woong Jung, Seoul (KR); Se Hee Hwang, Seoul (KR); Jin Hee Lee, Seoul (KR); Kang-Pyo Lee, Seoul (KR); Kwang Woo Hwang, Seoul (KR); Tae Joon Won, Seoul (KR)

(73) Assignee: CJ CHEILJEDANG CORP., Seoul (KR)

( * ) Notice: Subject to any disclaimer, the term of this patent is extended or adjusted under 35 U.S.C. 154(b) by 60 days.

This patent is subject to a terminal disclaimer.

(21) Appl. No.: 16/148,569

(22) Filed: Oct. 1, 2018

(65) Prior Publication Data

US 2019/0091271 A1 Mar. 28, 2019

Related U.S. Application Data

(63) Continuation of application No. 14/832,214, filed on Aug. 21, 2015, now Pat. No. 10,130,666, which is a continuation of application No. 13/386,459, filed on Jan. 23, 2012, now abandoned, which is a continuation of application No. PCT/KR2009/004930, filed on Sep. 2, 2009.

(30) Foreign Application Priority Data

Jul. 22, 2009 (KR) ........................ 10-2009-0067015

(51) Int. Cl.

| | |
|---|---|
| *A23K 10/16* | (2016.01) |
| *A23K 10/18* | (2016.01) |
| *A23L 33/00* | (2016.01) |
| *A23L 33/135* | (2016.01) |
| *A61K 8/99* | (2017.01) |
| *A61K 35/74* | (2015.01) |
| *A61K 35/747* | (2015.01) |
| *A61P 1/04* | (2006.01) |
| *A61P 35/00* | (2006.01) |
| *A61P 37/04* | (2006.01) |
| *A61P 37/06* | (2006.01) |
| *A61P 37/08* | (2006.01) |
| *A61P 43/00* | (2006.01) |
| *A61Q 19/00* | (2006.01) |
| *C12N 1/20* | (2006.01) |
| *C12R 1/225* | (2006.01) |
| *C12R 1/25* | (2006.01) |

(52) U.S. Cl.
CPC ............ *A61K 35/747* (2013.01); *A23K 10/18* (2016.05); *A23L 33/135* (2016.08); *A61K 8/99* (2013.01); *A61K 35/74* (2013.01); *A61Q 19/00* (2013.01); *C12R 1/25* (2013.01); *A23V 2002/00* (2013.01); *A23Y 2220/67* (2013.01)

(58) Field of Classification Search
None
See application file for complete search history.

(56) References Cited

U.S. PATENT DOCUMENTS

| | | | |
|---|---|---|---|
| 5,948,651 | A | 9/1999 | Doherty et al. |
| 6,761,885 | B1 | 7/2004 | Hakansson et al. |
| 6,977,086 | B1 | 12/2005 | Barges et al. |
| 9,314,041 | B2 | 4/2016 | Sashihara et al. |
| 2004/0047849 | A1 | 3/2004 | Hsu et al. |
| 2005/0053694 | A1 | 3/2005 | Byun et al. |
| 2006/0088513 | A1 | 4/2006 | Inoue et al. |
| 2006/0094056 | A1 | 5/2006 | Chappell et al. |
| 2009/0269321 | A1 | 10/2009 | Sashihara et al. |

FOREIGN PATENT DOCUMENTS

| | | |
|---|---|---|
| EP | 1134600 A1 | 9/2001 |
| EP | 1880726 A1 | 1/2008 |
| JP | 2006-519759 A | 8/2006 |
| KR | 10-1999-0008403 A | 1/1999 |
| KR | 10-2003-0064462 A | 8/2003 |
| KR | 10-2004-0023755 A | 3/2004 |
| KR | 10-2007-0078107 A | 7/2007 |
| KR | 10-2010-0063500 A | 6/2010 |
| KR | 10-2010-0063503 A | 6/2010 |
| WO | WO 2007/108763 A1 | 9/2007 |

OTHER PUBLICATIONS

Hirose et al., "Daily Intake of Heat-Killed Lactobacillus plantarum L-137 Augments Acquired Immunity in Healthy Adults", Journal of Nutrition, Nutritional Immunology, pp. 3069-3073, 2006.
KR 2001-000390 A Kwon (Jan. 2001)—English language abstract only.
Lappin et al. (Blood Reviews, vol. 14, pp. 228-239; 2000).
Niedzielin et al. (European Journal of Gastroenterology and Hepatology, vol. 13, No. 10, pp. 1143-1147; 2001).
Pochard et al., "Lactic acid bacteria inhibit TH2 cytokine production by mononuclear cells from allergic patients," Journal Allergy and Clinical Immunology, vol. 110, No. 4, pp. 617-623 (2002).
Rymarchyket. al., Immunology, vol. 125, pp. 331-343 (2008).

*Primary Examiner* — Soren Harward
*Assistant Examiner* — Paul D. Pyla
(74) *Attorney, Agent, or Firm* — Birch, Stewart, Kolasch & Birch, LLP

(57) ABSTRACT

The present invention provides *Lactobacillus plantarum* CJLP133 KCTC 11403BP, a composition for treating intestinal diseases comprising the lactic acid bacteria, and a composition for enhancing immunity comprising the lactic acid bacteria.

4 Claims, 28 Drawing Sheets

Specification includes a Sequence Listing.

```
SEQUENCE LISTING

<160> NUMBER OF SEQ ID NOS: 1

<210> SEQ ID NO 1
<211> LENGTH: 1486
<212> TYPE: DNA
<213> ORGANISM: Lactobacillus plantarum

<400> SEQUENCE: 1
agtcgaacga actctggtat tgattggtgc ttgcatcatg atttacattt gagtgagtgg      60
cgaactggtg agtaacacgt gggaaacctg cccagaagcg ggggataaca cctggaaaca     120
gatgctaata ccgcataaca acttggaccg catggtccga gtttgaaaga tggcttcggc     180
tatcactttt ggatggtccc gcggcgtatt agctagatgt tgaggtaacg gctcaccatg     240
gcaatgatac gtagccgacc tgagagggta atcggccaca ttgggactga gacacggccc     300
aaactcctac gggaggcagc agtagggaat cttccacaat ggacgaaagt ctgatggagc     360
aacgccgcgt gagtgaagaa gggtttcggc tcgtaaaact ctgttgttaa agaagaacat     420
atctgagagt aactgttcag gtattgacgg tatttaacca gaaagccacg gctaactacg     480
tgccagcagc cgcggtaata cgtaggtggc aagcgttgtc cggatttatt gggcgtaaag     540
cgagcgcagg cggttttttta agtctgatgt gaaagccttc ggctcaaccg aagaagtgca     600
tcggaaactg gaaacttga gtgcagaaga ggacagtgga actccatgtg tagcggtgaa     660
atgcgtagat atatggaaga acaccagtgg cgaaggcggc tgtctggtct gtaactgacg     720
ctgaggctcg aaagtatggg tagcaaacag gattagatac cctggtagtc cataccgtaa     780
acgatgaatg ctaagtgttg gagggtttcc gcccttcagt gctgcagcta acgcattaag     840
cattccgcct ggggagtacg gccgcaaggc tgaaactcaa aggaattgac ggggcccgc     900 acaagcggtg gagcatgtgg tttaattcga agctacgcga agaaccttac caggtcttga     960
catactatgc aaatctaaga gattagacgt tcccttcggg gacatggata caggtggtgc    1020
atggttgtcg tcagctcgtg tcgtgagatg ttgggttaag tcccgcaacg agcgcaaccc    1080
ttattatcag ttgccagcat taagttgggc actctggtga gactgccggt gacaaaccgg    1140
aggaaggtgg ggatgacgtc aaatcatcat gccccttatg acctgggcta cacacgtgct    1200
acaatggatg gtacaacgag ttgcgaactc gcgagagtaa gctaatctct taaagccatt    1260
ctcagttcgg attgtaggct gcaactcgcc tacatgaagt cggaatcgct agtaatcgcg    1320
gatcagcatg ccgcggtgaa tacgttcccg ggccttgtac acaccgcccg tcacaccatg    1380
agagtttgta acacccaaag tcggtgggt aacctttag gaaccagccg cctaaggtgg    1440
gacagatgat tagggtgaag tcgtaacaag tatgccgttg cccccc                  1486
```

LACTOBACILLUS PLANTARUM AND COMPOSITION COMPRISING SAME

CROSS REFERENCE TO RELATED APPLICATIONS

This application is a Continuation of U.S. application Ser. No. 14/832,214 filed on Aug. 21, 2015, which is a Continuation of U.S. application Ser. No. 13/386,459 filed Jan. 23, 2012, which is a Continuation of PCT Application No. PCT/KR2009/004930 filed on Sep. 2, 2009, which claims priority to Korean Application No. KR 10-2009-0067015 filed in the Republic of Korea on Jul. 22, 2009. The contents of all of which are hereby expressly incorporated herein by reference, in their entirety, into the present application.

TECHNICAL FIELD

The present invention relates to a novel *Lactobacillus plantarum*, and compositions comprising the same. More particularly, the present invention relates to a novel *Lactobacillus plantarum* helpful for the prevention/treatment of an enteric disease and an immune disease and a composition comprising the same.

BACKGROUND ART

Lactic acid bacteria which can be found in traditional fermented food such as 'Kimchi' is in a symbiotic relationship with human within the digestive tract, and digests fibers and composite protein. These microorganisms contribute to the digestive environment within human or other animals and named 'probiotics'. These probiotics should have good acid-resistance, bile acid-resistance and intestinal epithelial cell-adherence in order to be efficiently attached to the small intestine when taken orally.

The *Lactobacillus* sp. is a representative bacteria that is found in traditional fermented food such as 'Kimchi'. *Lactobacillus* sp. are rod shaped bacteria which are found within the gastrointestinal tract of human or other animals, dairy products and vegetables, and causes homo- or hetero-fermentation. *Lactobacillus* sp. lowers the pH of the gastrointestinal tracts to depress the reproduction of harmful bacteria such as *E. coli* or *Clostridium*, and improves diarrhea or constipation. Also, these bacteria have a role for vitamin synthesis, anticarcinogenic activities, lowering of cholesterol levels. Acidophillin which is a product of the lactic acid bacteria activity, also depresses the growth of *Shigella, Salmonella, Staphylococcus, E. coli*. Furthermore, lactic acid bacteria improves diarrhea by depressing the growth of the bacteria responsible for diarrhea and normalisation of intestinal flora. (Michael and Phillipe, Probiotics and prebiotics: Effects on diarrhea, The journal of nutrition, Volume 137, March 2007, pages 803S-811S; Roberfroid, Prebiotics and probiotics: Are the functional foods?, American journal of clinical nutrition, Volume 71, June 2000, pages 1682S-1687S).

At present there are increasing amount of research on developing probiotics and feedstuff using previously mentioned characteristics of the *Lactobacillus* sp. Bacteria-caused diarrhea in livestocks leads to the decrease of rate of gain and increase of mortality rate. Therefore, in order to prevent this occurring, adding antibiotics in the feeds have been generally accepted. However, the use of antibiotics in feeds is being further regulated and organic livestock husbandry is recommended due to problems occurring from antibiotic resistant-bacteria and the antibiotic-remains within the animals. (Korean patent Laid-Open publication 1998-78358) (McEwen and Fedorka-Cray, Antimicrobial use and resistance in animals, Clinical infectious Disease, Volume 34, June 2002, pages S93-S106).

Furthermore, *Lactobacillus* sp. is known to be effective in increasing the immune response. Recently, immune diseases such as allergy or atopic disease are increasing globally including Korea. Currently in Europe, bacteriotherapy aiming to cure these diseases by orally administering lactic acid bacteria is ongoing. Research describes that *Lactobacillus rhamnosus* had decreased the incidence rate of atopic disease in children (Kalliomaki et al., Probiotics in primary prevention of atopic disease: a randomised placebo-controlled trial, Lancet, Volume 357, April 2001, pages 1076-1079). Also, it has been reported that the area and degree of eczema had decreased in children with progressed atopy when they were treated with *Lactobacillus rhamnosus* and *Lactobacillus reuteri* (Rosenfeldt et al., Effect of probiotic *Lactobacillus* strains in children with atopic dermatitis, Dermatologic and ocular diseases, Volume 111, February 2003, pages 389-395).

Although the exact mechanism of the increased immune effect of the lactic acid bacteria has not been revealed, the research aiming to understand the cause is currently ongoing and so far it is understood that the orally administered lactic acid bacteria inhabits within the gastrointestinal tract and influence the immune system. For example, it has been reported that lactic acid bacteria from yogurt increases the activity of Peyer's patch lymphocytes, and stimulates IgA response shown from experiments with both animals and human. In addition, lactic acid bacteria affects both innate and adaptive immune system. These bacteria kills the pathogenic bacteria in the gastrointestinal tract (innate immunity), and also activates the macrophages which destroy and present the antigen to the T lymphocyte (adaptive immunity) producing various cytokines and interleukins such as IL-12 and IL-18. The increased secretion of cytokines is a result of the activation of NF-κB and STAT signalling pathway in the macrophages stimulated by the cell wall components of the lactic acid bacteria. Moreover, lactic acid bacteria are professional antigen presenting cells and activate dendritic cells in the lymph nodes and gastrointestinal mucous membranes resulting in secretion of increased levels of IL-12, IL-18 and TNFα. Furthermore, these bacteria also increase the membrane proteins of the dendritic cells which activates MHC class II and B7-2 which stimulates T lymphocytes (Cross et al., Anti-allergy properties of fermented foods: an important immunoregulatory mechanism of lactic acid bacteria?, International Immunopharmacology, Volume 1, May 2001, pages 891-901).

T lymphocytes are essential in adaptive immune immunity and it is comprised of the cell-mediated Th1 and antibody-mediated Th2 responses. During the Th1 response, production of cytokines from antigen presenting cells such as IL-2, IL-18, and Interferon (IFN) are dominant. But during the Th2 response, PGE2, IL-4 and IL-10 are dominant. The balance between these two responses is important and various immune diseases may occur when the balance is interrupted. Th1 cells are mostly involved with infection where Th2 cells are associated with allergic and inflammatory responses. In the case which Th2 cells are over activated, the production of IgE antibodies increases, and may cause allergic responses to some proteins (pollen, food) which were not as harmful before. Therefore, it is important that Th1 and Th2 responses remain balanced as instability may cause disease. In addition, it has been reported that the secretion of cortisol occurring from continuous stress may cause cancer, atopy, allerty and autoimmune diseases, as in this case Th1 response decreases and Th2 response increases (Elenkov and Chrousos, Stress hormones, Th1/Th2 patterns, pro/anti-inflammatory cytokines and susceptibility to disease, Trends in Endocrinology and Metabolism, Volume 10, November 1999, pages 359-368).

It has been reported from an in vivo experiment that lactic acid bacteria increases the secretion of IFN-γ which is a Th1 cell cytokine, but depresses the secretion of IL-4 and IL-5 which are Th2 cell cytokines (Matsuzaki et al., The effect of oral feeding of *Lactobacillus casei* strain Shirota on immunoglobulin E production in mice, Journal of Dairy Science, Volume 81, January 1998, pages 48-53). Also, another experiment described that administration of lactic acid bacteria into ovalbumin-primed mice which shows a biased Th2 response resulted in increased level of IFN-γ but decreased levels of IL-4, IL-5 and IgE. Furthermore, co-culture of spleen cells collected from these animals with lactic acid bacteria caused the same pattern of cytokine production as the in vivo experiment. However, the co-culture of T lymphocytes with lactic acid bacteria did not show the increase of IFN-γ suggesting that antigen presenting cells such as macrophages or dendritic cells may be necessary for the production of IFN-γ from T lymphocytes (Kato et al., Lactic acid bacterium potently induces the production of interleukin-12 and interferon-gamma by mouse splenocytes, International Journal of Immunopharmacology, Volume 21, February 1999, pages 121-131). Furthermore, it has been reported that the secretion of IL-12 and IL-18 which are cytokines produced from macrophages or dendritic cells increased dose-dependently, when these cells were co cultured with lactic acid bacteria. Therefore, lactic acid bacteria balance the Th1/Th2 responses where Th2 response is dominant, by stimulating the Th1 response and increasing IL-12 and IL-18 production (Cross et al., Anti-allergy properties of fermented foods: an important immunoregulatory mechanism of lactic acid bacteria?, International Immunopharmacology, Volume 1, May 2001, pages 891-901). Thus, lactic acid bacteria is beneficial for preventing or treating cancer, atopy, allergy and autoimmune diseases which is caused by the unbalance of Th1/Th2 responses and Th2 dominant responses.

Figure 1:
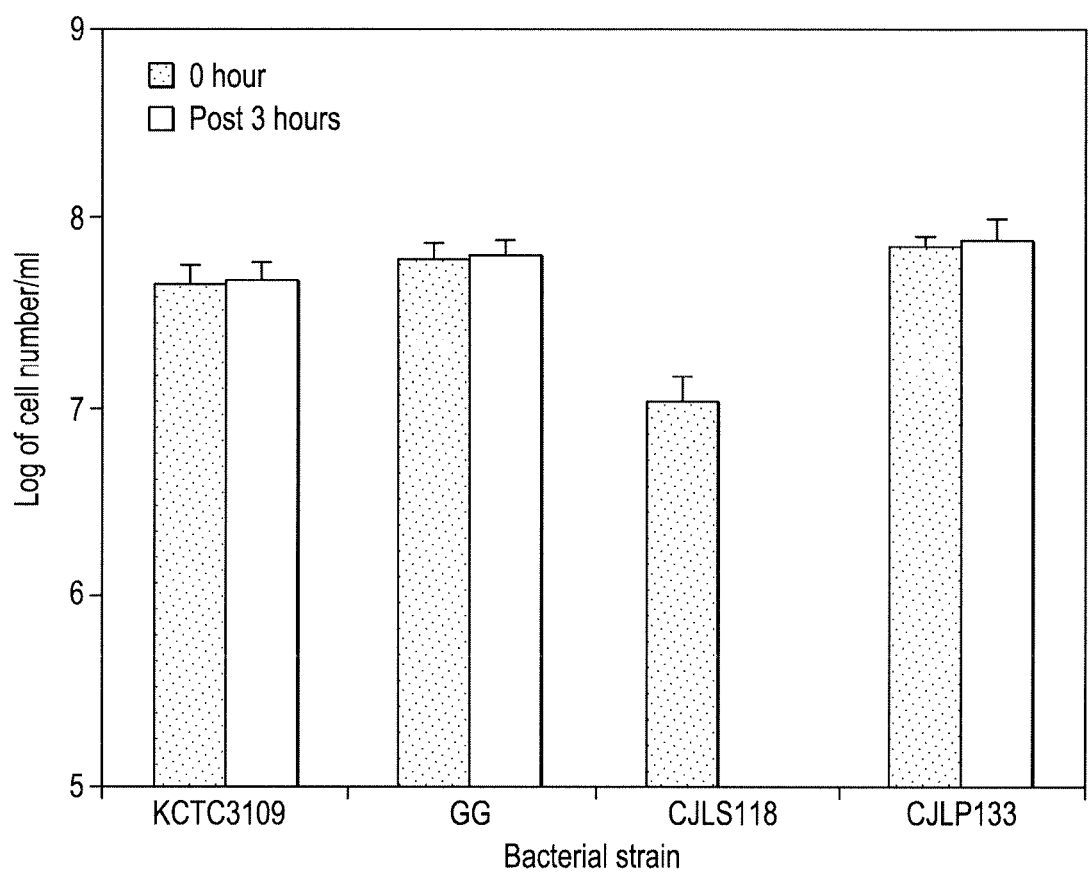
FIG. 1 shows a graph illustrating the acid-resistance of *Lactobacillus plantarum* CJLP133.

The inventors separated and identified a novel strain of *Lactobacillus* sp. from traditional fermented food in order to develop a bacteria more efficient for controlling the imbalance of Th1/Th2 response caused from excessive Th2 response, than other known bacteria.

Therefore, the aim of the invention is to develop a novel strain of *Lactobacillus* sp. which has excellent acid-resistance, bile acid-resistance, intestinal epithelial cell-adherence and induce improved immune response, especially by balancing the Th1/Th2 response where excessive Th2 response occurs.

The other aim of the present invention is to provide a composition composed of the mentioned novel strain of *Lactobacillus* sp. which is beneficial for the prevention or the treatment of enteric diseases.

Another aim of the present invention is to provide a composition composed of the mentioned novel strain of *Lactobacillus* sp. which is beneficial for improving immune responses.

In order to achieve the mentioned aim, present invention provides *Lactobacillus plantarum CJLP*133 (Deposited at the Korea Research Institute of Bioscience and Biotechnology (KRIBB), located at 111 Gwahangno, Yuseong-gu, Daejeon 305-806, Republic of Korea on Oct. 9, 2008, Accession number: KCTC 11403BP).

Furthermore, present invention provides a composition composed of *Lactobacillus plantarum* CJLP133, which is beneficial for the prevention or the treatment of enteric diseases.

In addition, present invention provides a composition composed of *Lactobacillus plantarum* CJLP133, which is beneficial for the improving immune responses. The detailed description of the present invention follows below.

*Lactobacillus plantarum* CJLP133 is characterised as a novel strain of *Lactobacillus plantarum* which was separated and identified from traditional fermented food. The mentioned traditional fermented food are kimchi, fermented vegetables, soybean paste, soy sauce, fast-fermented bean paste and salted fish, but not only limited to these.

The present *Lactobacillus plantarum* CJLP133 was 99.9% homologous with the reference strain (*Lactobacillus plantarum* NBRC15891™, GenBank accession number AB326351) showing highly molecular phylogeny confirmed by 16S rRNA sequencing. Therefore, mentioned microorganism has been identified as *Lactobacillus plantarum*, named as *Lactobacillus plantarum* CJLP133 and has been deposited at the Korea Research Institute of Bioscience and Biotechnology (KRIBB) on Oct. 9, 2008 (Deposit number KCTC 11403BP). The 16S rRNA sequencing result of *Lactobacillus plantarum* CJLP133 is SEQ ID NO1 in the Sequence Listing.

*Lactobacillus plantarum* CJLP133 in the present invention is a gram positive bacteria which is a facultative anaerobe, able to grow in both aerotropic and anaerobic conditions. This bacteria is immotile, rod-shaped and does not form spores. The detailed morphological and physiological characteristics of *Lactobacillus plantarum* CJLP133 are listed in Table 1 according to the common criteria of this technical field.

TABLE 1

| Morphological, physiological and biochemical characteristics | Results |
|---|---|
| Morphology | Rod |
| Motility | − |
| Spore | − |
| Catalase | − |
| Homo-hetero fermentation | Facultative fermentation |
| Proliferation at 15° C. | + |
| Proliferation at 45° C. | − |
| Proliferation at 3% NaCl | + |
| Anaerobic proliferation | + |
| $CO_2$ production with glucose | − |
| Sugar fermentation characteristics | |
| Glycerol | − |
| Erythritol | − |
| D-arabinose | − |
| L-arabinose | − |
| Ribose | + |
| L-arabinose | − |
| Ribose | + |
| D-xylose | − |
| L-xylose | − |
| Adonitol | − |
| Xyloside | − |
| Galactose | + |
| D-glucose | + |
| D-fructose | + |
| D-mannose | + |
| L-sorbose | − |
| Rhamnose | − |
| Dulcitol | − |
| Inositol | − |
| Mannitol | + |
| Sorbitol | + |
| D-mannoside | − |
| D-glucoside | − |
| Glucosamine | + |
| Amygdalin | + |
| Arbutin | − |
| Esculin | + |
| Salicin | + |
| Cellobiose | + |
| Maltose | + |
| Lactose | + |
| Melibiose | + |
| Saccharose | + |
| Trehalose | + |
| Innulin | − |
| Melizitose | + |
| D-raffinose | + |
| Amidon | − |
| Glycogen | − |
| Xylitol | − |

TABLE 1-continued

| Morphological, physiological and biochemical characteristics | Results |
|---|---|
| Gentiobiose | + |
| D-turanose | − |
| D-lyxose | − |
| D-tagatose | − |
| D-fucose | − |
| L-fucose | − |
| D-arabitol | − |
| L-arabitol | − |
| Gluconate | − |
| 2 Gluconate | − |
| 5-Gluconate | − |

+: Positive reaction
−: Negative reaction

In order to store *Lactobacillus plantarum* CJLP133 for a long period safely, it is recommended to keep the bacteria in preservation liquid mixed with water and glycerol at −70° C. or in suspension in sterilised 10% skimmed milk followed by lyophilisation.

Furthermore, *Lactobacillus plantarum* CJLP133 in the present invention is probiotics, which is beneficial for intestinal cleansing and improved immune responses like other lactic acid bacteria.

In the present invention, 'probiotics' is a term understood as a live microorganism which is beneficial for improving the gastrointestinal environment within human and other animals, therefore contributing to the host's health. Probiotics are live microorganisms with probiotic activity, and are beneficial for gut microbiota when delivered to human or animals as mixed or single bacterial strain in a dried or fermented form. In order to be an efficient probiotic microorganism, it is important that firstly these bacteria are able to pass through the stomach without the influence of gastric fluid and bile, so that the bacteria reaches and survives at the intestine to contribute to the health of gut microbiota. Therefore these bacteria must have acid-resistance, bile acid-resistance, and intestinal epithelial cell-adherence. Secondly, these bacteria should be safe microorganisms, and safety assessments are performed using gelatine liquefaction test, phenylalanine deaminase test, ammonification test and hemolysis test. *Lactobacillus plantarum* CJLP133 in the present invention has excellent acid-resistance, bile acid-resistance and intestinal epithelial cell-adherence. Also, *Lactobacillus plantarum* CJLP133 showed a negative result for gelatine liquefaction test, phenylalanine deaminase test and ammonification test, and showed α-hemolysis for hemolysis test proving the safety.

*Lactobacillus plantarum* CJLP133 in the present invention is predicted to be beneficial for intestinal health as it has excellent acid-resistance, bile acid-resistance and intestinal epithelial cell-adherence. Thus, in another aspect, this invention provides a composition composed of *Lactobacillus plantarum* CJLP133 which is beneficial for the prevention or treatment of enteric diseases.

The mentioned composition composed of *Lactobacillus plantarum* CJLP133 which is beneficial for the treatment or prevention of enteric diseases can be used for mammals including human and preferably for livestocks such as cows, horses, pigs. The mentioned 'enteric diseases' include infection of the gastrointestinal tract and inflammatory enteric diseases. For example, infectious diarrhea caused by pathogenic microorganisms (*E. coli, Salmonella, Clostridium*), gastroenteritis, inflammatory enteric diseases, neurogenic colitis, overgrowth of microorganism in small intestine, acute gastroenteritis are included but only limited to these. The mentioned *Lactobacillus plantarum* CJLP133 used for the present composition is preferred to be alive, although it can be either used alive or killed. In general, live bacteria cures and improves any symptoms caused by abnormal fermentation by gut microorganisms, and prevents harmful bacteria from adhering to the intestinal walls when administered in human or animals. Also, live bacteria produces lactate which works toward decreasing the intestinal pH, hence preventing the survival of the harmful bacteria. Furthermore, the administered live bacteria prevents the proliferation of harmful bacteria and helps the activity of intestinal vili which absorbs nutrients by producing bacteriocin and peroxide. In addition, live bacteria is beneficial for producing material which helps the absorption of nutrients and its use, improves the demand rate of feedstuff, and neutralise toxic compounds secreted from pathogenic bacteria.

The administration route of the present compound described in this invention is recommended to be through oral methods, although it is not limited. The dose differs depending on the type of enteric disease, the degree of symptoms, age, gender, race, purpose of administration (treatment or prevention), however, ten million to 100 billion bacteria can be administered in adults in general.

Furthermore, *Lactobacillus plantarum* CJLP133 is not only beneficial for the intestinal health but also accelerates immune responses noticeably compared with other lactic acid bacteria. *Lactobacillus plantarum* CJLP133 increases the secretion of IL-12 inducing Th1 response in the spleen, and also suppresses the secretion of IL-4 which induces the Th2 response. Also, *Lactobacillus plantarum* CJLP133 stimulates the antigen presenting cells which regulate the T cell immune response such as macrophage and dendritic cells. These antigen presenting cells then secretes cytokines which induces the differentiation of Th1 cell from the cells so that the imbalance of Th1/Th2 is compensated, therefore proving the fact that *Lactobacillus plantarum* CJLP133 has the ability for immune regulation. More detailed description of the increased immune response caused by *Lactobacillus plantarum* CJLP133 is explained below.

*Lactobacillus plantarum* CJLP133 produced 7.3 to 9.5 times more IL-12 which induces the Th1 response, and suppressed the production of IL-4 which induces Th2 response by 3.2 to 12.1% compared with negative controls. The cytokines were measured from the splenocyte of a mouse treated with ovalbumin so that Th2 response is dominant. The immune regulatory effect of *Lactobacillus plantarum* CJLP133 is superior to other lactic acid bacteria such as *Lactobacillus rhamnosus* (KCTC 5033), *Lactobacillus casei* (KCTC3109), *Lactobacillus sakei* CJLS118 (KCTC13416). Therefore *Lactobacillus plantarum* CJLP133 has immune regulatory properties as it balances the imbalance of Th1/Th2 response by suppressing the Th2 response and stimulating the Th1 response.

In addition, it has been confirmed that *Lactobacillus plantarum* CJLP133 improves immune responses by stimulating macrophages, shown by experiments coculturing *Lactobacillus plantarum* CJLP133 with macrophages (RAW264.7) and dendritic cells (JAWS II). When *Lactobacillus plantarum* CJLP133 was cocultured with macrophages (RAW264.7) and dendritic cells (JAWS II), the secretion of IL-12 and IL-18 which both induces the differentiation of Th1 cells were increased but the secretion of IL-10 which inhibits the differentiation of Th1 cells was depressed compared to IL-12. This experiment also proves that *Lactobacillus plantarum* CJLP133 CJLP133 has immune regulatory properties as it balances the imbalance of Th1/Th2 response by stimulating the Th1 response.

IL-4 is secreted from Th2 cells which is essential for cellular immunity and is an anti-inflammatory cytokine which suppresses the secretion of IL-12 from Th1 cells. Recently reports have described that the amount of Th2 cells secreting IL-4 and IL-5 were increased in the blood and skin lesions of patients with atopic dermatitis (Miraglia et al., Immune dysregulation in atopic dermatitis, Allergy and Asthma Proceedings, Volume 27, November-December 2006, pages 451-455). Therefore, domination of Th2 response and imbalance of Th1/Th2 response may cause diseases such as atopic dermatitis. Also, as it has been described earlier, the imbalance of Th1/Th2 response may cause illness. Diseases such as cancer, atopic dermatitis, allergy and autoimmune disease may occur when Th1 response is decreased and Th2 response is increased (Elenkov and Chrousos, Stress hormones, Th1/Th2 patterns, pro/anti-inflammatory cytokines and susceptibility to disease, Trends in Endocrinology and Metabolism, Volume 10, November 1999, pages 359-368). Hence, *Lactobacillus plantarum* CJLP133 may be used for the treatment of not only atopic dermatitis, allergy by its immune regulatory properties balancing Th1/Th2 responses, but also for the treatment of cancer or autoimmune diseases.

Therefore, in another aspect, present invention provides a composition composed of *Lactobacillus plantarum* CJLP133, which is beneficial for increasing immune responses. This composition is effective for increasing immune responses due to the activity of *Lactobacillus plantarum* CJLP133 within. Also, this composition is effective for the prevention or treatment of diseases caused by the imbalance of Th1/Th2 response and dominant Th2 response, due to the activity of *Lactobacillus plantarum* CJLP133 within. Hence, the present composition composed of *Lactobacillus plantarum* CJLP133 can be used for the prevention or treatment of atopic dermatitis, allergy, cancer and autoimmune diseases. Autoimmune diseases such as asthma and hay fever could be prevented or treated but not only limited to these.

The administration route of the present composition composed of *Lactobacillus plantarum* CJLP133 is recommended to be through oral methods, but not limited to this. The dose differs depending on the type of enteric disease, the degree of symptoms, age, gender, race, purpose of administration (treatment or prevention), however, ten million to 100 billion bacteria can be administered in adults in general.

The described composition composed of *Lactobacillus plantarum* CJLP133 which is beneficial for prevention or treatment of enteric diseases and increasing immune responses, is free from side effects for use as medicine, health functional food, cosmetics, feedstuff, and feed additives, as it includes lactic acid with proven safety.

In the case that the described composition composed of *Lactobacillus plantarum* CJLP133 is used as medical substance, the composition can be manufactured into conventional pharmaceutically acceptable carriers. This composition can be manufactured into an oral dosage form preferably. For example, liquid form, suspension concentrate, powder form, granule form, tablet, capsule, pills or extract forms could be used for administration.

In formulating into a respective dosage form, pharmaceutically acceptable and required carriers or additives may be added in manufacturing the dosage form. For example, at least one carrier selected from diluents, slip agents, binding agents, disintegrating agents, sweetening agents, stabilizers and preservative agents; and at least one additive selected from flavouring agents, vitamins and antioxidants may be used in formulating the oral dosage forms.

Any pharmaceutically acceptable carriers and additives may be used. Specifically, it may be preferable that lactose, corn starch, soybean oil, microcrystalline cellulose or mannitol is used as diluents; magnesium stearate or talc is used as slip agents; polyvinylpyrrolidone or hydroxypropylcellulose is used as binding agents. Further, it may be preferable that carboxymethylcellulose calcium, sodium starch glycolate, polacrilin potassium or crospovidone is used as disintegrating agents; white sugar, fructose, sorbitol or aspartame is used as sweeting agents; sodium carboxymethylcellulose, β-cyclodextrin, white wax or xanthan gum is used as stabilizers; and methyl ρ-hydroxybenzoate, propyl ρ-hydroxybenzoate or potassium solvate is used as preservative agents.

Further, in addition to the above ingredients, natural herbs with Mae-sil (Japanese apricot) flavor, lemon flavor, pineapple flavor or herb flavor, natural fruit juice, natural pigments such as chlorophyllin or flavonoid, sweeting ingredients such as fructose, honey, sugar alcohol or sugar, acidifiers such as citric acid or sodium citrate may be used after mixing for a purpose of raising appetite.

Formulating methods and carriers and additives necessary for such formulating are detailed in Remington's Pharmaceutical Sciences (19th ed., 1995).

Furthermore, the present composition composed of *Lactobacillus plantarum* CJLP133 can be used as food. The food composition covers conventional daily-consumed general foods as well as health foods. If the food composition is used in the health foods, it may be formulated into conventional health food dosage forms known to the art, with sitologically acceptable carriers or additives. The health foods may be formulated, for example, into powder, granule, tablet, capsule, suspension, emulsion, syrup, liquid, extract, jelly or drink form. As sitologically acceptable carriers or additives, an arbitrary carrier or additive usable in any forms to prepare may be used.

The present composition can also be used as cosmetics as it is beneficial for the prevention and treatment of atopic dermatitis. The cosmetic composition according to the present invention may be formulated into conventional form known to the cosmetic industries. Any carrier or additive which is acceptable and necessary in manufacturing a specific cosmetic form may be added.

The present composition can also be used as feed additives or feedstuff.

Used in the feed additives, the composition may be manufactured into a form of 20 to 90% highly concentrated liquid, powders or granules. The feed additive may additionally include at least one selected from organic acids such as citric acid, humalic acid, adipic acid, lactic acid and malic acid; phosphates such as sodium phosphate, potassium phosphate, acidic pyrophosphates and polyphosphates (condensed phosphate); and natural antioxidants such as polyphenols, catechins, alpha-tocopherols, rosemary extracts, vitamin C, green tea extracts, licorice extracts, chitosan, tannic acids and phytic acids. Used in the feed composition, the composition may be manufactured into a conventional animal feed form and include conventional feed ingredients.

The feed additives and the animal feed may additionally include crops, for example, crushed or shredded wheat, oats, barley, corn and rice; vegetable protein feeds, for example, feeds mainly consisting of rape, soybean and sunflower; animal protein feeds, for example, blood meal, meat meal, bone meal and fish meal; and sugar and dairy products, for example, various dry ingredients consisting of milk powder and whey powder, and may further include nutritional supplements, digestion- and absorption-enhancers and growth promoters.

The feed additives may be administered to animals individually or in combination with other additives selected from edible carriers. Further, the feed additives may be topdressing, may be directly mixed with animal feeds or may be easily administered to animals as oral dosage forms separately from animal feeds. In case of being administered separately from animal feeds, the feed additives may be combined with pharmaceutically acceptable edible carriers and prepared into immediate-release formulations or sustained-release formulations, as well known in the art. The edible carriers may be solid or liquid, for example, corn starch, lactose, sucrose, soy flake, peanut oil, olive oil, sesame oil and propylene glycol. In case solid carriers are used, the feed additives may be in a form of tablet, capsule, powder, troche or lozenge, or may be a not-dispersed topdressing. If liquid carriers are used, the feed additives may have a form of soft gelatin capsules, syrup, suspension, emulsion or solution.

The feeds may include an arbitrary protein-containing organic grain flour which has been conventionally used to meet animals' appetite. The protein-containing grain flour typically consists of corn or soybean flour or is a mix of corn/soybean flour.

In addition, the feed additives and the animal feeds may contain adjuvants such as preservatives, stabilizers, wetting agents, emulsifiers and liquefying agent. The feed additives may be added to animal feeds by means of dipping, spraying or mixing for use.

The animal feeds or feed additives according to the present invention may be applied to a diet for various animals such as mammals, poultry and fish. The mammals may be pets (for example, dogs, cats) as well as pigs, cows, sheep, goats and laboratory rodents; poultry such as chickens, turkeys, ducks, geese, pheasant and quail; and fish such trout, without limitation thereto.

As described above, *Lactobacillus plantarum* CJLP133 according to the present invention is a probiotics which is characterised by acid-resistance, bile acid-resistance, intestinal epithelial cell-adherence. This bacteria is also beneficial for the intestinal health and balances the imbalance of Th1/Th2 response caused by excessive Th2 response by stimulating Th1 response. Therefore, the novel *Lactobacillus plantarum* CJLP133 according to the present invention can be used in a composition for treatment of enteric diseases and for increasing the immune response, and for treatment or prevention of diseases caused by imbalance of Th1/Th2 response.

Hereinafter, the present invention will be described by the following examples in more detail. However, the purpose of these examples is only to illustrate the present invention, not to limit the scope of the invention thereto in any way.

EXAMPLE 1: ISOLATION AND IDENTIFICATION OF MICROORGANISM *LACTOBACILLUS PLANTARUM CJLP*133 BACTERIA

Lactic acid bacteria *Lactobacillus plantarum* CJLP133 were streaked onto solid MRS medium (Difco, USA) containing 1.5% agar and incubated at 30° C. for 24 hrs. Colonies confirmed as being purely separated were taken by a loop and incubated with MRS broth (Difco, USA) at 30° C. for 18 to 24 hrs.

Then, the morphology and physiological properties of *Lactobacillus plantarum* CJLP133 bacteria were determined with API50CH and API50CHL kits (Bio-Me'reux) according to the methods disclosed in Kim et. al., *Leuconostoc inhae* sp. nov., a lactic acid bacterium isolated from kimchi, International Journal of Systematic and Evolutionary Microbiology, Volume 53, July 2003, pages 1123-1126. The resultant morphology and physiological properties of *Lactobacillus plantarum* CJLP133 bacteria were summarized in the above table 1.

Further, a sequence of 16S rRNA gene was analyzed for identification and classification of the lactic acid bacteria. The sequence of 16S rRNA gene was determined and analyzed according to a method disclosed in Kim et. al., *Leuconostoc kimchii* sp. nov., a new species from kimchi. International Journal of Systematic and Evolutionary Microbiology, Volume 50, September 2000, pages 1915-1919. The sequencing result of CJLP133 is listed in sequence list SEQ ID NO1.

Since *Lactobacillus plantarum* CJLP133 according to the present invention has the highest homology (99.9%) with *Lactobacillus plantarum* NBRC 15891™ reference bacteria (GenBank accession number AB326351), *Lactobacillus plantarum* CJLP133 according to the present invention was identified as *Lactobacillus plantarum*, named as *Lactobacillus plantarum* CJLP133 and deposited to Korea Research Institute of Bioscience and Biotechnology (KRIBB) Oct. 9, 2008 (Accession number: KCTC 11403BP).

EXAMPLE 2: EXPERIMENT INVESTIGATING ACID-RESISTANCE AND BILE ACID-RESISTANCE OF *LACTOBACILLUS PLANTARUM* CJLP133 USING ARTIFICIAL GASTRIC JUICE AND ARTIFICIAL BILE

The acid-resistance experiment was performed using the artificial gastric juice modified and made referring to an experiment from Kobayashi et al (Kobayashi et al., Studies on biological characteristics of *Lactobacillus*: II. Tolerance of the multiple antibiotic resistance strain, *L. casei* PSR3002, to artificial digestive fluids. Japan Journal of Microbiology, Volume 29, July 1974, pages 691-697). In detail, the artificial gastric juice was made by adjusting the pH of MRS liquid medium to pH 2.5 using 1N HCl and adding 100 unit/ml of pepsin followed by sterilisation.

The isolated *Lactobacillus plantarum* CJLP133 as described in Example 1 was cultured in MRS liquid medium at 37° C. for 18 hours and then centrifuged for precipitation. Then the precipitation was washed with sterilised 0.85% NaCl twice. Then $10^7$ cfu/ml of the bacterial suspension was inoculated on the control medium and artificial gastric juice for further culture at 37° C. The total number of live bacteria was estimated at 0 and 3 hour-post inoculation after diluting bacteria by ten times in phosphate buffer including $KH_2$, $PO_4$, $Na_2HPO$, L-cysteine, HCl, Tween 80.

The bile acid-resistance experiment was performed using the artificial bile modified and made referring to an experiment from Casey et al (Casey et al., Isolation and characterisation of anti-*Salmonella* lactic acid bacteria from the porcine gastrointestinal tract, Letters in Applied Microbiology, Volume 39, 2004, pages 431-438). Bacteria was cultured on the MRS liquid medium added with 0.3% bile of bull, and the total number of bacteria was counted after 0, 12 and 24 hours post-inoculation of the lactic acid bacteria likewise to the acid resistance-experiment.

The described acid-resistance and bile acid-resistance were also tested on other representative lactic acid bacteria such as *Lactobacillus casei* (KCTC3109), *Lactobacillus sakei* CJLS118 (KCTC 13416) and *Lactobacillus rhamnosus* GG (KCTC 5033), for comparison.

Figure 2:
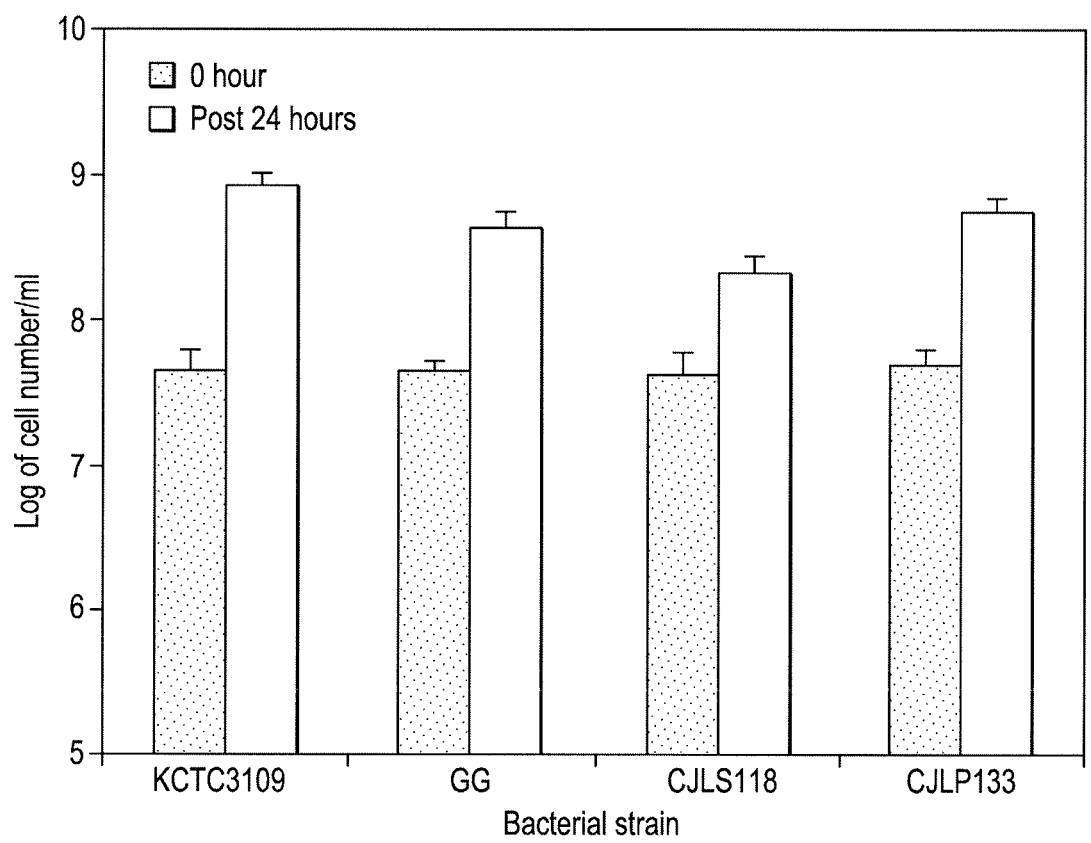
FIG. 2 shows a graph illustrating the bile acid-resistance of *Lactobacillus plantarum* CJLP133.

The results are illustrated in FIG. 1 and FIG. 2. FIG. 1 shows a graph illustrating the acid-resistance of *Lactobacillus plantarum* CJLP133. FIG. 2 shows a graph illustrating the bile acid-resistance of *Lactobacillus plantarum* CJLP133.

According to the results illustrated in FIG. 1 and FIG. 2, *Lactobacillus plantarum* CJLP133 showed more acid-resistance and bile acid-resistance compared with other lactic acid bacteria. This shows that the novel bacteria described in this invention is capable of reaching and surviving at the intestine without being influenced by the gastric juice or bile at the intestine.

EXAMPLE 3: EXPERIMENTS TESTING INTESTINAL EPITHELIAL-ADHERENCE OF *LACTOBACILLUS PLANTARUM* CJLP133

Animal cell line HT-29 was provided by the Korean Cell Line Bank (KCLB) in order to test intestinal epithelial-adherence, and the methods were used described in the research of Kim et al and Hirano et al (Kim et al., Probiotic properties of *Lactobacillus* and *Bifidobacterium* strains isolated from porcine gastrointestinal tract, Applied Microbiology and Biotechnology, Volume 74, April 2007, pages 1103-1111, Hirano et al., The effect of *Lactobacillus rhamnosus* on enterohemorrhagic *Escherichia coli* infection of human intestinal cells in vitro, Microbiology and Immunology, Volume 47, 2003, pages 405-109).

HT-29 was cultured in RPMI 1640 (Gibco, USA) medium added with heat deactivated 10% Fetal Bovine Serum, 1% L-Glutamine, penicillin G (100 IU/mL) and streptomycin (100 mg/mL) at 5% $CO_2$, 37° C. In order to test adherence and detachment, $1.0 \times 10^5$ cell/ML of HT-29 cells were plated on wells of a 24 well plate. The medium were exchanged every other day for culture of these cells until there was a complete monolayer settled. Complete monolayers of HT-29 were washed 5 times with 25° C. of PBS buffer and RPMI1640 medium without antibiotics was added.

$1.0 \times 10^9$ of *Lactobacillus plantarum* CJLP133 were suspended in RPMI and inoculated in each wells to be cultured for 2 hours at 5% $CO_2$, 37° C. After the culture, the wells were washed with PBS buffer three times by stirring the plate at 200 rpm for 3 minutes, in order to remove any detaching lactic acid bacteria and to test adherence properties. After the wash, 0.2% trypsin-EDTA was added to detach any cells from the wells. The number of bacteria which was streak plated on MRS-agar plate was counted using serial dilution method with peptone number after being cultured at 37° C. for 24 hours.

Also, in order to test the partial adherence properties of the lactic acid bacteria, same amount of the lactic acid bacteria used in the experiment above was placed on top of HT-29 cells which were cultured on a cover glass sterilised with 70% alcohol for a day placed on a petri dish. The number of lactic acid bacteria which were adhered to HT-29 cells was counted by looking under the light microscope after being dried and stained by Gram staining. Comparison experiments were performed using *Lactobacillus sakei* CJLS118 (KCTC 13416) and *Lactobacillus rhamnosus* GG (KCTC 5033).

Figure 3:
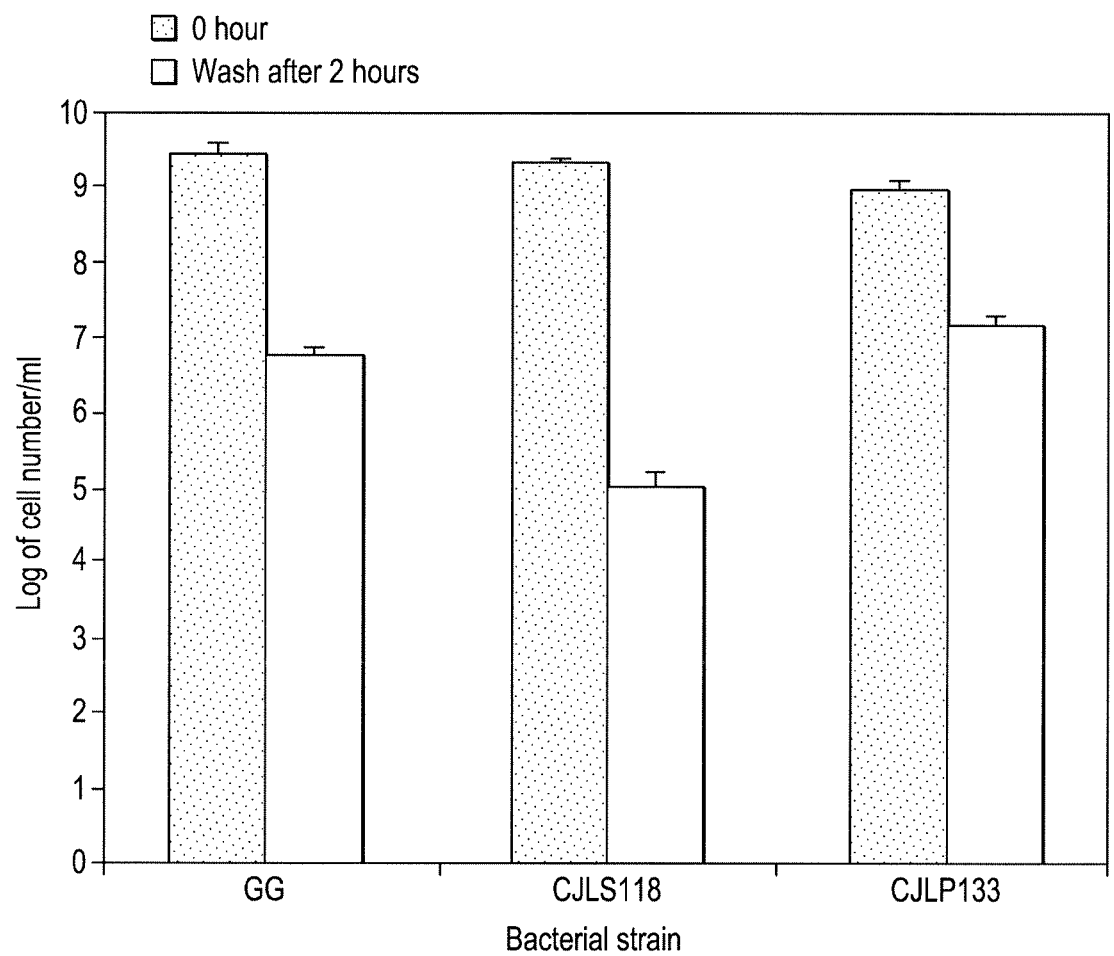
FIG. 3 shows a graph illustrating the intestinal epithelial cell-adherence properties of *Lactobacillus plantarum* CJLP133.

The results are illustrated in FIG. 3. FIG. 3 shows a graph illustrating the intestinal epithelial cell-adherence properties of *Lactobacillus plantarum* CJLP133. The results illustrated in FIG. 3 shows that *Lactobacillus plantarum* CJLP133 has better intestinal epithelial-adherence measured after 24 hours than other probiotics such as *Lactobacillus rhamnosus* GG (KCTC 5033) and *Lactobacillus sakei* CJLS118 (KCTC 13416). Especially, the adherence properties of *Lactobacillus plantarum* CJLP133 was much better than *Lactobacillus sakei* CJLS118 (KCTC 13416). These results suggest that the novel bacterial strain indicated in this invention could improve the intestinal health by adhering to intestinal epithelia.

EXAMPLE 4: SAFETY ASSESSMENT OF *LACTOBACILLUS PLANTARUM* CJLP133

Hemolysis test, gelatin liquefaction test, hazardous metabolite (ammonification) test and phenylalanine deaminase test were performed according to the safety assessment methods suggested by the standard of Korea Biotechnology Industry Organization to assess safety of the bacteria isolated from the Example 1. The obtained result is summarized in table 2.

TABLE 2

Safety assessment for *Lactobacillus plantarum* CJLP133

| | Tests | | | |
|---|---|---|---|---|
| Bacteria | gelatin liquefaction | phenylalanine deaminase | hemolysis | ammonification |
| CJLP133 | negative | negative | α-hemolysis, safe | negative |

Based on the above result, *Lactobacillus plantarum* CJLP133 was found negative in the gelatin liquefaction test, hazardoug metabolite (ammonification) test, phenylalanine deaminase test. Hemolysis test showed α-hemolysis which is irrelevant with pathogenic bacteria. Accordingly, *Lactobacillus plantarum* CJLP133 was confirmed as being safe for administration to a human being.

EXAMPLE 5: EVALUATION OF STIMULATING PROPERTIES OF IL-12 PRODUCTION AFTER TREATING MOUSE SPLENOCYTE

*Lactobacillus plantarum* CJLP133 was added to mouse splenocytes treated with ovalbumin biased towards Th2 response, in order to evaluate the stimulating properties of *Lactobacillus plantarum* CJLP133 inducing IL-12 production which is a Th1 response inducing cytokine. For the experiment, methods were referred from reports from Fujiwara et al. (Fujiwara et al., A double-blinded trial of *Lactobacillus paracasei* strain KW3110 administration for immunomodulation in patients with pollen allergy, Allergology International, 2005, volume 54, pages 143-149) and Fujiwara et al. (Fujiwara et al., The anti-allergic effects of lactic acid bacteria are strain dependent and mediated by effects on both Th1/Th2 cytokine expression and balance, International Archives of Allergy and Immunology, 2004, Volume 135, pages 205-215).

5 of 6 weeks old female Balb/c mouse were immunised with a mixed solution composed of 1.538 mL of 13 mg/mL alumhydroxide (Sigma), 10 mg ovalbumin, 0.4615 mL of PBS. This solution was mixed well and kept at room temperature for 20 minutes for reaction, and 0.2 mL (1 mg OVA+2 mg alum) was injected peritoneally into the mouse.

The same amount of solution was injected into these mice on day 6 post injection, for boosting. Mice were sacrificed on day 13 post injection to remove the spleen. 100 µl (4×106) splenocytes taken from the spleen, 50 µl of killed bacteria for testing and 50 µl (4 mg/ml) of ovalbumin were added and placed onto cell culture well plate in DMEM-10 medium for 7 days at 10% $CO_2$ for culture. After the 7 days culture, the supernatant fluid was taken for measuring IL-12 concentrations using IL-12 ELISA kit (Biosource).

The killed bacteria for testing described above were obtained as written below.

The test bacteria was inoculated in MRS liquid medium (Difco) and cultured for 24 hours at 37° C. Then the culture medium was centrifuged at 13000 rpm for 1 minute followed by 2 times of washing using physiological saline, and the bacteria was obtained. The obtained bacteria was heated at 100° C. for 10 minutes suspended in sterilised distilled water (same amount as the original culture medium). Then the suspension was centrifuged at 13000 rpm for 1 minute and the bacteria was resuspended in DMEM medium at the concentration of 50 µg/ml and 5 µg/ml. Test bacteria was *Lactobacillus plantarum* CJLP133, and the same experiment was performed using *Lactobacillus rhamnosus* GG (KCTC 5033), *Lactobacillus casei* (KCTC 3109) and *Lactobacillus sakei* CJLS118 (KCTC 13416) for comparison.

The mentioned IL-12 assay was performed by using IL-12 ELISA kit and provided instructions. The O.D value of the control sample provided within the kit was measured and referring to the equation, the amount of IL-12 from the samples was calculated. The results are illustrated in FIG. 4.

Figure 4:
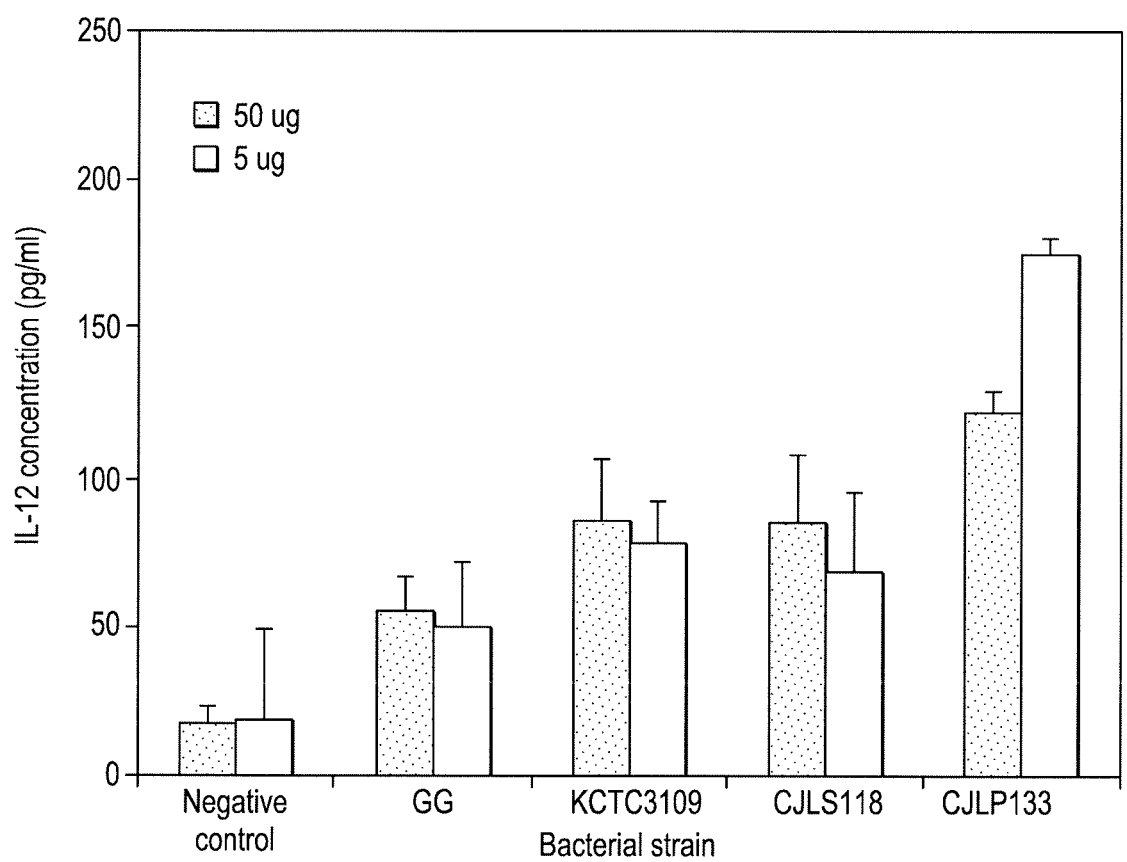
FIG. 4 shows a graph illustrating the concentrations of IL-12 which is a cytokine inducing Th1 response from a mouse splenocyte. This splenocyte was pre-treated with ovalbumin which induces Th2 response and was then co cultured with *Lactobacillus plantarum* CJLP133 and also with other bacteria for comparison of IL-12 measurement.

FIG. 4 shows a graph illustrating the concentrations of IL-12 which is a cytokine inducing Th1 response from a mouse splenocyte. This splenocyte was pre-treated with ovalbumin which induces Th2 response and was then co cultured with *Lactobacillus plantarum* CJLP133 and also with other bacteria for comparison of IL-12 measurement.

According to the result shown in FIG. 4, *Lactobacillus plantarum* CJLP133 markedly induces the production of IL-12 which is a Th1 response inducing cytokine, compared to other bacteria. Therefore, it has been proved that *Lactobacillus plantarum* CJLP133 in this invention efficiently induces Th1 response in mouse with biased Th2 response.

EXAMPLE 6: EVALUATION OF SUPPRESSION OF IL-4 PRODUCTION AFTER TREATMENT WITH MOUSE SPLENOCYTE

In order to test whether *Lactobacillus plantarum* CJLP133 suppresses the production of IL-4 which is a Th2 response inducing cytokine, *Lactobacillus plantarum* CJLP133 was added to mouse splenocyte biased with Th2 response due to ovalbumin treatment. ELISA kit was used as has been described in Example 5, but IL-4 kit (Biosource) was used instead of IL-12 kit. Other experimental conditions were the same and the results are shown in FIG. 5.

Figure 5:
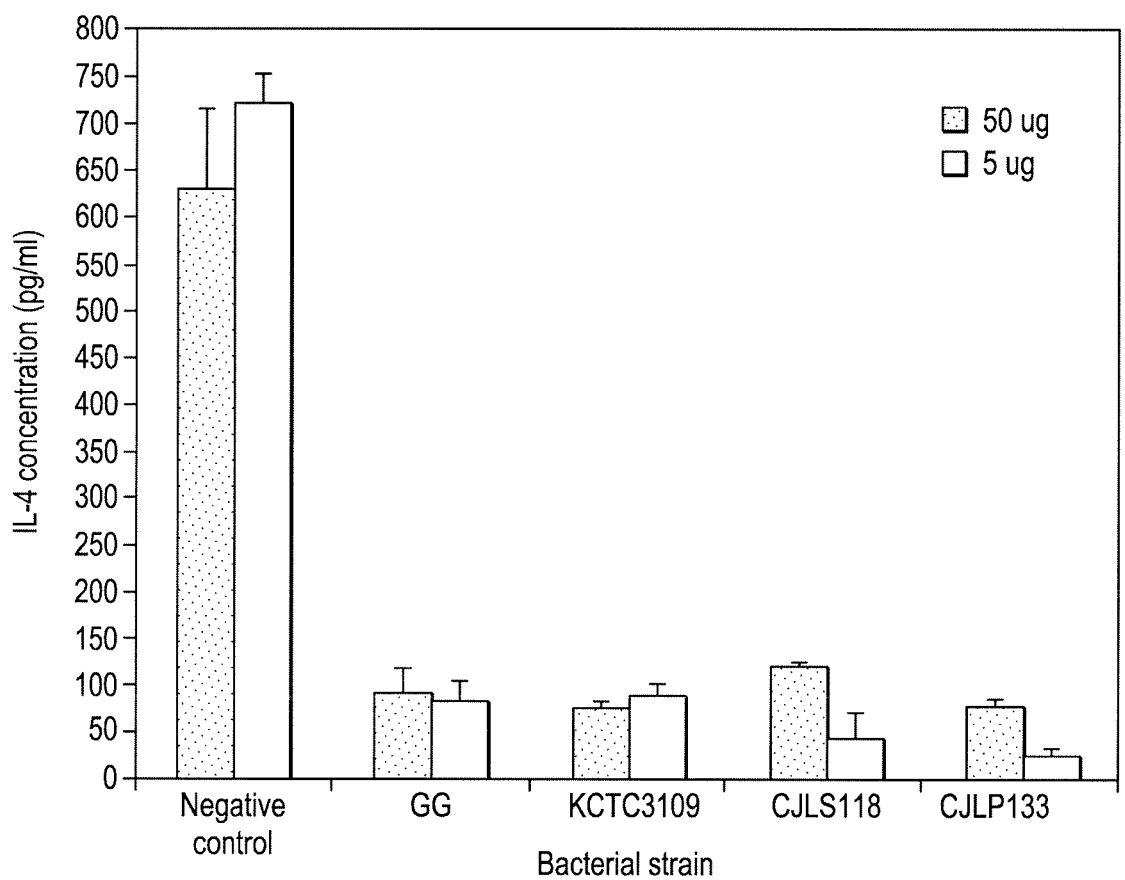
FIG. 5 shows a graph illustrating the concentrations of IL-4 which is a cytokine inducing Th2 response from a mouse splenocyte. This splenocyte was pre-treated with ovalbumin which induces Th2 response and was then co cultured with *Lactobacillus plantarum* CJLP133 and also with other bacteria for comparison of IL-4 measurement.

FIG. 5 shows a graph illustrating the concentrations of IL-4 which is a cytokine inducing Th2 response from a mouse splenocyte. This splenocyte was pre-treated with ovalbumin which induces Th2 response and was then co cultured with *Lactobacillus plantarum* CJLP133 and also with other bacteria for comparison of IL-4 measurement.

FIG. 5 shows that *Lactobacillus plantarum* CJLP133 suppresses the production of IL-4, a cytokine that induces Th2 response, so that it suppresses Th2 response in mouse splenocytes biased towards Th2 response.

EXAMPLE 7: EXPERIMENTS TESTING THE EXPRESSION OF CYTOKINES IL-12P40 AND IL-18 WHICH INDUCES THE DIFFERENTIATION INTO TH1 LYMPHOCYTE, AND EXPRESSION OF CYTOKINE IL-10 WHICH SUPPRESSES THE DIFFERENTIATION INTO TH1 LYMPHOCYTES

Antigen presenting cells such as macrophages and dendritic cells produce IL-12 and IL-18 which induces the differentiation of Th1 cells from Th0 cells, and on the other hand produce IL-10 which suppresses the differentiation of Th1 cells from Th0 cells. Further experiments were performed in order to investigate the effect of lactic acid bacteria on the production of IL-12, IL-10 and IL-18 by macrophages and dendritic cells.

$5 \times 10^7$/mL of test bacteria was added to macrophage cell line RAW264.7 and cultured for 48 hours at 37° C., 10% $CO_2$. Then the medium was taken to measure the concentrations of IL-12p40 and IL-10 using ELISA method. Also the bacteria was added to dendritic cell line JAWS II using the same method as above, and the concentrations of IL-12p40 and IL-10 were measured using ELISA.

The test bacteria was *Lactobacillus plantarum* CJLP133, and lipopolysaccharide was used as a positive control. *Lactobacillus rhamnosus* GG (KCTC 5033), *Lactobacillus casei* (KCTC 3109) and *Lactobacillus sakei* CJLS118 (KCTC 13416) were also used in the experiment to compare the results.

Measurement of concentrations of cytokines was performed using ELISA method. IL-12p40 kit (BD BioSciences, USA) and IL-10 kit (BD BioSciences, USA) was used for measurement of IL-12 and IL-10 respectively. The results are illustrated in FIG. 6 and FIG. 7.

Figure 6:
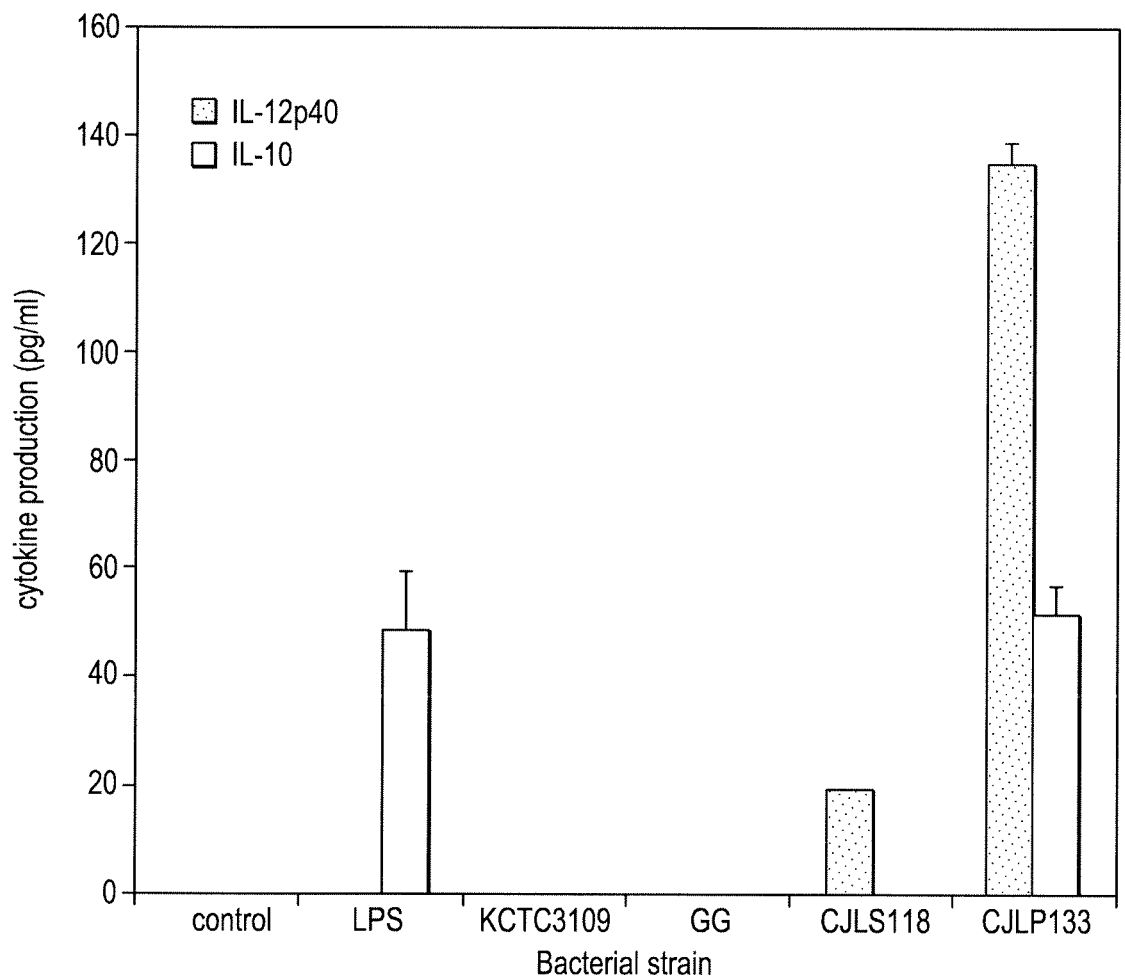
FIG. 6 shows a graph illustrating the concentrations of IL-12 and IL-10 using ELISA from macrophage cell line RAW264.7 treated with *Lactobacillus plantarum* CJLP133 compared with other types of lactic acid bacteria.

FIG. 6 shows a graph illustrating the concentrations of IL-12 and IL-10 using ELISA from macrophage cell line RAW264.7 treated with *Lactobacillus plantarum* CJLP133 compared with other types of lactic acid bacteria.

Figure 7:
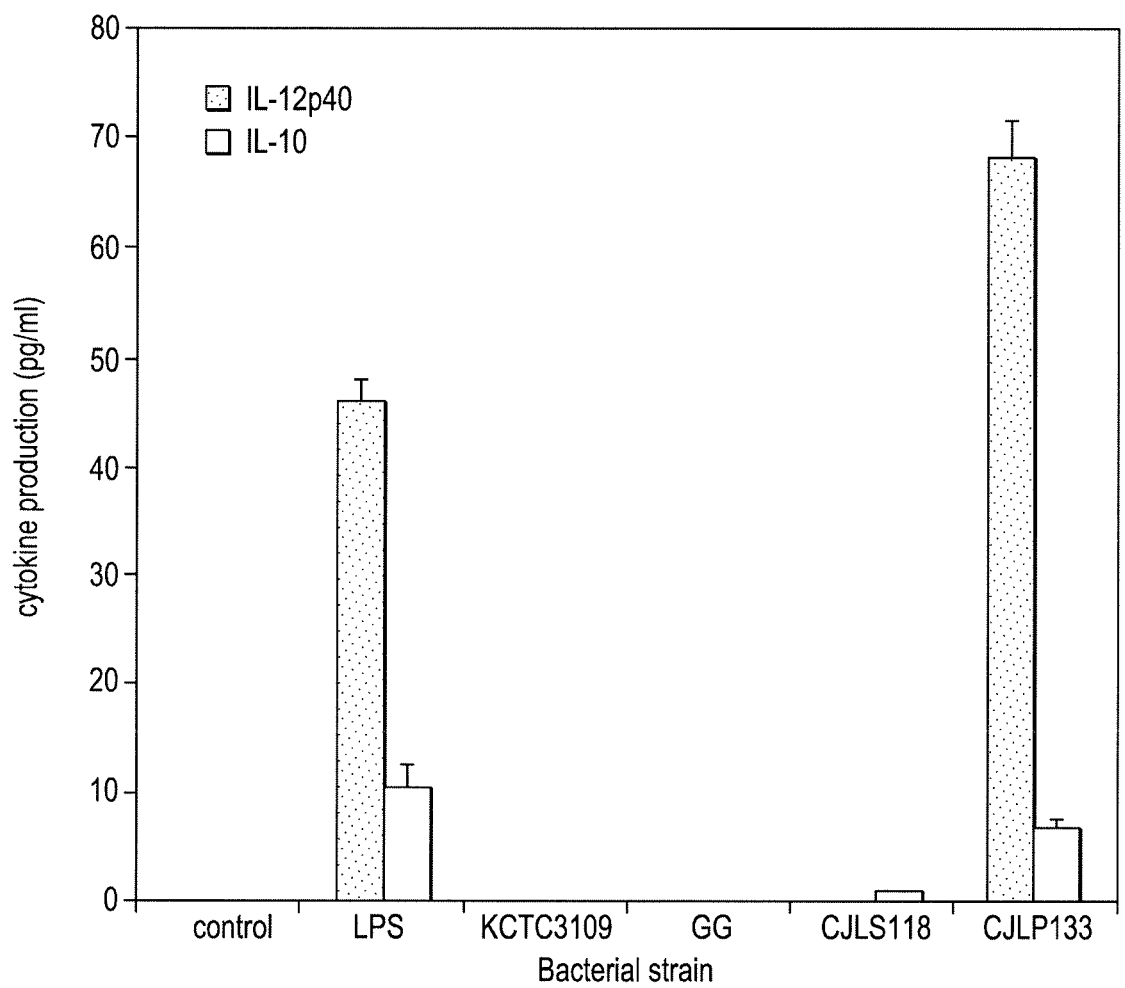
FIG. 7 shows a graph illustrating the concentrations of IL-12 and IL-10 using ELISA from dendritic cell line JAWS II treated with *Lactobacillus plantarum* CJLP133 compared with other types of lactic acid bacteria.

FIG. 7 shows a graph illustrating the concentrations of IL-12 and IL-10 using ELISA from dendritic cell line JAWS II treated with *Lactobacillus plantarum* CJLP133 compared with other types of lactic acid bacteria.

According to the results illustrated in FIG. 6 and FIG. 7, *Lactobacillus plantarum* CJLP133 produces IL-12 which is a cytokine that induces the differentiation into Th1, and produces less IL-10 which is a cytokine that suppresses the differentiation into Th1, compared with IL-12. Also *Lactobacillus plantarum* CJLP133 produces a more noticeable amount of IL-12 than other lactic acid bacteria.

Furthermore, in order to investigate the amount of IL-12 and IL-18 at a genetic level, $5 \times 10^7$/mL of test bacteria was added to macrophage cell line RAW264.7 for culture at 37° C., 10% $CO_2$ for 6 hours. Then the total RNA was extracted and the mRNA concentration of IL-12 and IL-18 was measured using RT-PCR. The test bacteria was also inoculated and cultured with dendritic cell line JAWS II in order to measure the mRNA amount of IL-12 and IL-18 using RT-PCR.

Figure 8:
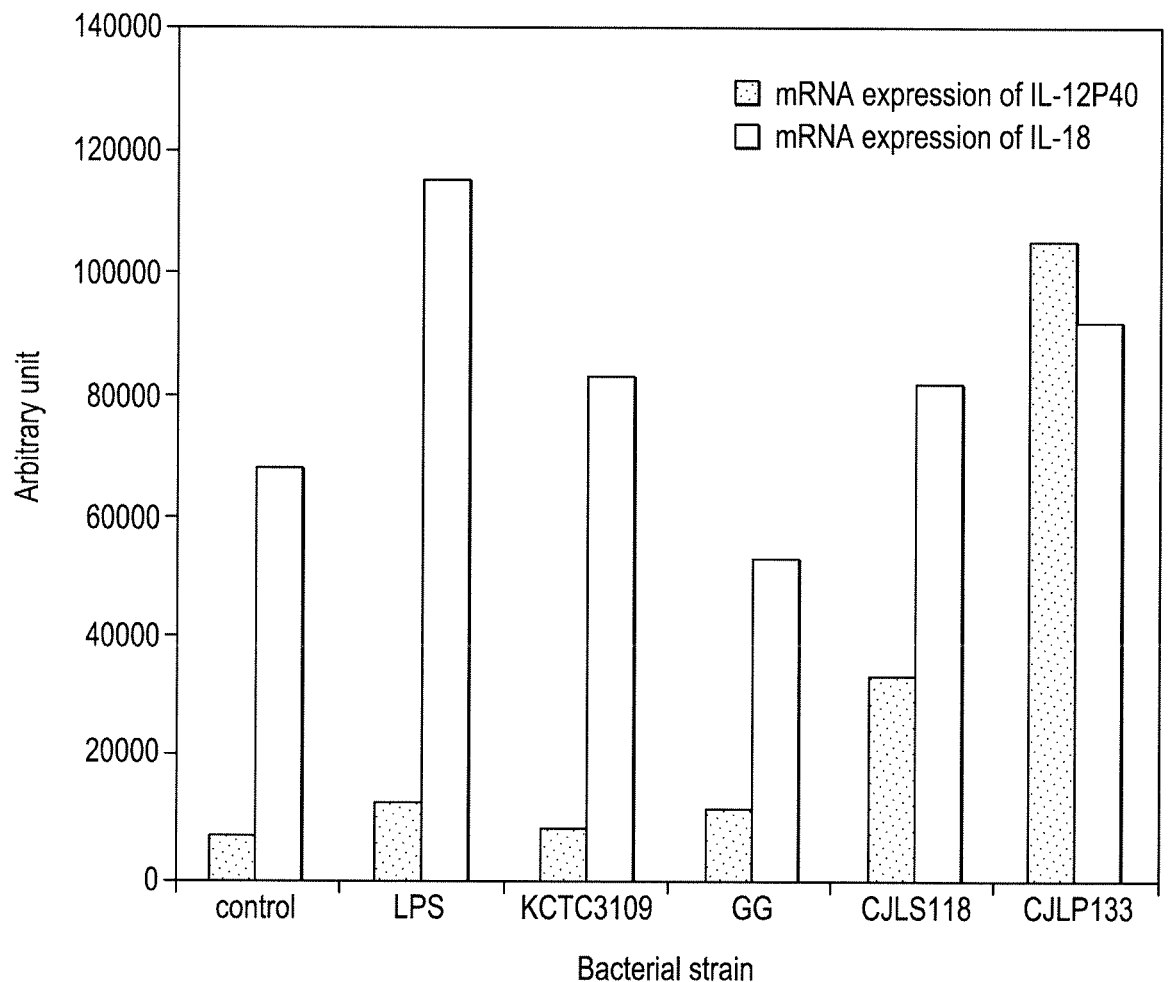
FIG. 8 shows a graph illustrating the mRNA concentrations of IL-12p40 and IL-18 using RT-PCR from macrophage RAW264.7 treated with *Lactobacillus plantarum* CJLP133 compared with other types of lactic acid bacteria.
Figure 9:
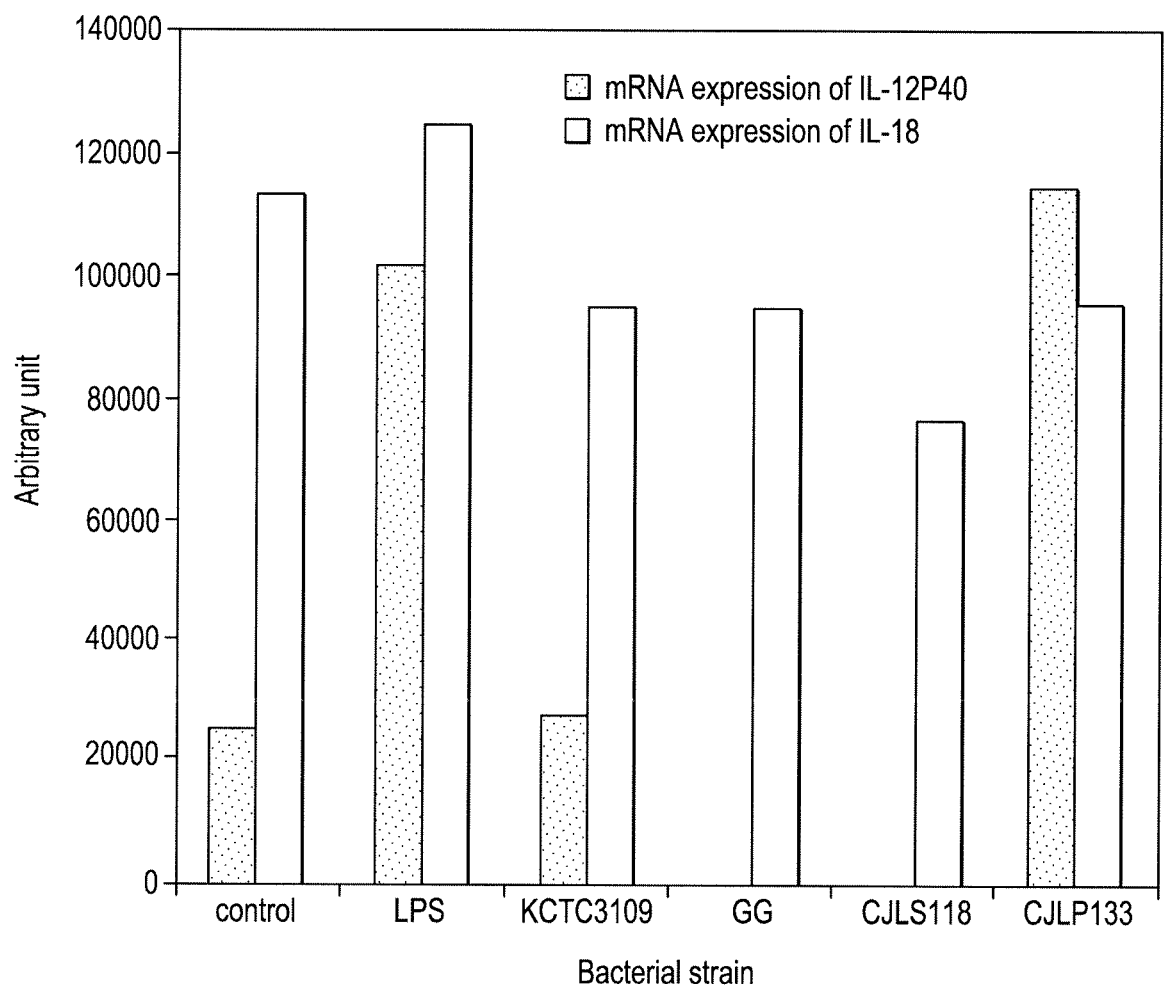
FIG. 9 shows a graph illustrating the mRNA concentrations of IL-12p40 and IL-18 using RT-PCR from dendritic cell JAWS II treated with *Lactobacillus plantarum* CJLP133 compared with other types of lactic acid bacteria.

The results are illustrated in FIG. 8 and FIG. 9.

FIG. 8 shows a graph illustrating the mRNA concentrations of IL-12p40 and IL-18 using RT-PCR from macrophage RAW264.7 treated with *Lactobacillus plantarum* CJLP133 compared with other types of lactic acid bacteria.

FIG. 9 shows a graph illustrating the mRNA concentrations of IL-12p40 and IL-18 using RT-PCR from dendritic cell JAWS II treated with *Lactobacillus plantarum* CJLP133 compared with other types of lactic acid bacteria.

According to the results illustrated in FIG. 8 and FIG. 9, *Lactobacillus plantarum* CJLP133 stimulates the production of mRNA inducing the formation of IL-12 and IL-18 which are cytokines that induce the differentiation into Th1 cells. Particularly, *Lactobacillus plantarum* CJLP133 produces more noticeable amount of IL-12 mRNA compared with other lactic acid bacteria.

EXAMPLE 8: IN VIVO EXPERIMENT OF THE EFFECT OF *LACTOBACILLUS PLANTARUM* CJLP133 STRAIN ON ATOPIC DERMATITIS

Experimental Animal Breeding and Grouping

Lactic acid bacterial strain was administered orally into NC/Nga mouse which were caged for a week after arriving at the animal unit as 4 weeks old. The temperature was kept at 24±2° C., and the light cycle was 12 hours. Feedstuff was in powder form without any antibiotics added. Lactic acid bacteria was administered orally into mice by mixing with feedstuff evenly for 10 weeks ($1 \times 10^{10}$ cfu/animal). Atopic dermatitis was induced in animals 6 weeks post administration of lactic acid bacteria, by applying Biostir AD ointment (Biostir, Japan) for 5 weeks. Mice were grouped as non induction group without induction of atopic dermatitis, control group induced with atopic dermatitis, a group with atopic dermatitis administered with lactic acid bacteria. 8 mice were used per each group (Table 3). *Lactobacillus sakei* CJLS118 (KCTC13416), *Lactobacillus rhamnosus* GG (KCTC 5033) were used as test lactic acid bacteria. Also, CJLP55 (KCTC11401BP), CJLP56 (KCTC 11402BP) and CJLP136 (KCTC 11404BP) which were developed by the applicant of the present invention were used. Lastly, CJLP133 (KCTC 11403BP) from the present invention was used as well.

TABLE 3

| Group | Administered lactic acid bacteria | Induction of atopic dermatitis |
|---|---|---|
| non-induction | | X |
| Control group | | ◯ |
| GG | GG (KCTC 5033) | ◯ |
| LP55 | CJLP55 (KCTC 11401BP) | ◯ |
| LP56 | CJLP56 (KCTC 11402BP) | ◯ |
| LP133 | CJLP133 (KCTC 11403BP) | ◯ |
| LP136 | CJLP136 (KCTC 11404BP) | ◯ |
| LS118 | CJLS118 (KCTC 13416) | ◯ |
| LA12 | CJLA12 | ◯ |

Induction of Atopic Dermatitis

Fur was removed from the back upto the back of the ear of NC/Nga mouse using a depilater and any remaining fur was removed using a depilatory cream. 4% SDS solution was sprayed on to the application area to remove the lipid component and dried for an hour. A flat stick was used to apply 100 mg of Biostir AD ointment (Biostir, Japan) at the back and the earflap evenly. The Biostir AD ointment was applied 10 times in total by applying twice per week for 5 weeks.

Tissue Staining

Atopic dermatitis is characterised by thickening of the skin, penetration of immune cells such as lymphocytes, monocytes, eosinophils, mast cells into the tissue causing inflammation. Also, the nerve fiber extends abnormally to the epidermis causing itchiness. Therefore, the skin of the mouse with atopic dermatitis was removed to examine and count the numbers of the immune cells and nerve fibers mentioned above.

Five weeks after inducing atopic dermatitis, the mouse was culled for removal of the skin. The skin was fixed with Accustain formali-free fixative solution and was paraffin blocked. The block was cut by 5 μm, and went under hematoxylin/eosin staining to check the thickness of the skin (epidermis+derma). The tissue was also used to investigate the accumulation of lymphocytes within the inflammatory lesion using the light microscope of the 2×2 mm area. Also, the tissue was stained with Toluidine blue to detect mast cells, and Congo red to detect eosinophils in the 2×2 mm area using light microscope. Mast cells and eosinophils were counted by looking at the area from the epidermis to the muscle tissue. Immunohistochemistry was used in order to detect the penetration of nerve fibers into the skin tissue. Anti-protein gene product (PGP.5) antibody was used for detection, and biotin-conjugated goat anti-rabbit antibody and peroxidise-conjugated streptavidin was added sequentially for colour formation by peroxidise reaction.

The results are illustrated in FIGS. 10A to 13B.

Figure 10A:
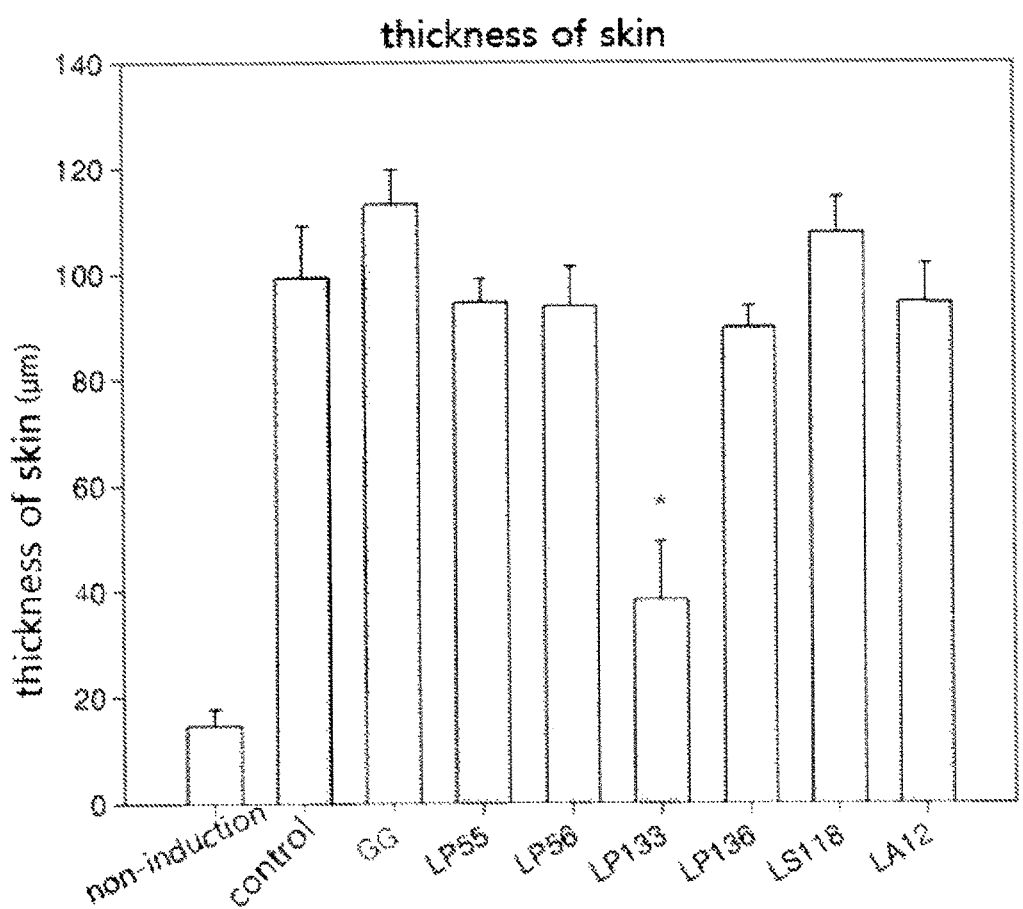
FIG. 10A shows the thickness of the skin removed from the NC/Nga mouse with atopic dermatitis which was treated with lactic acid bacteria.

FIG. 10A shows the thickness of the skin removed from the NC/Nga mouse with atopic dermatitis which was treated with lactic acid bacteria.

Figure 10B:
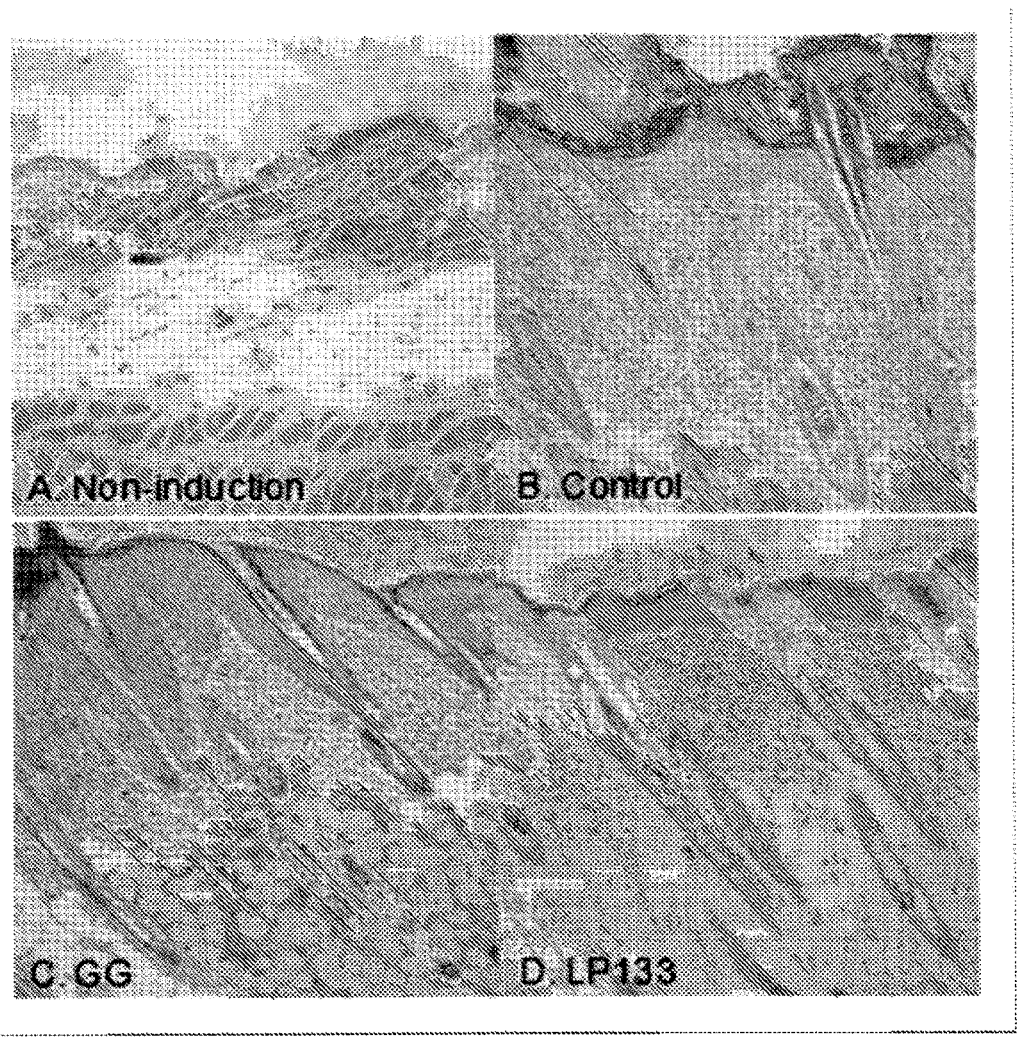
FIG. 10B shows the light microscopic photo of lymphocytes accumulated within the inflammatory lesion of the skin removed from the NC/Nga mouse with atopic dermatitis which was treated with lactic acid bacteria.

FIG. 10B shows the light microscopic photo of lymphocytes accumulated within the inflammatory lesion of the skin removed from the NC/Nga mouse with atopic dermatitis which was treated with lactic acid bacteria.

Figure 11A:
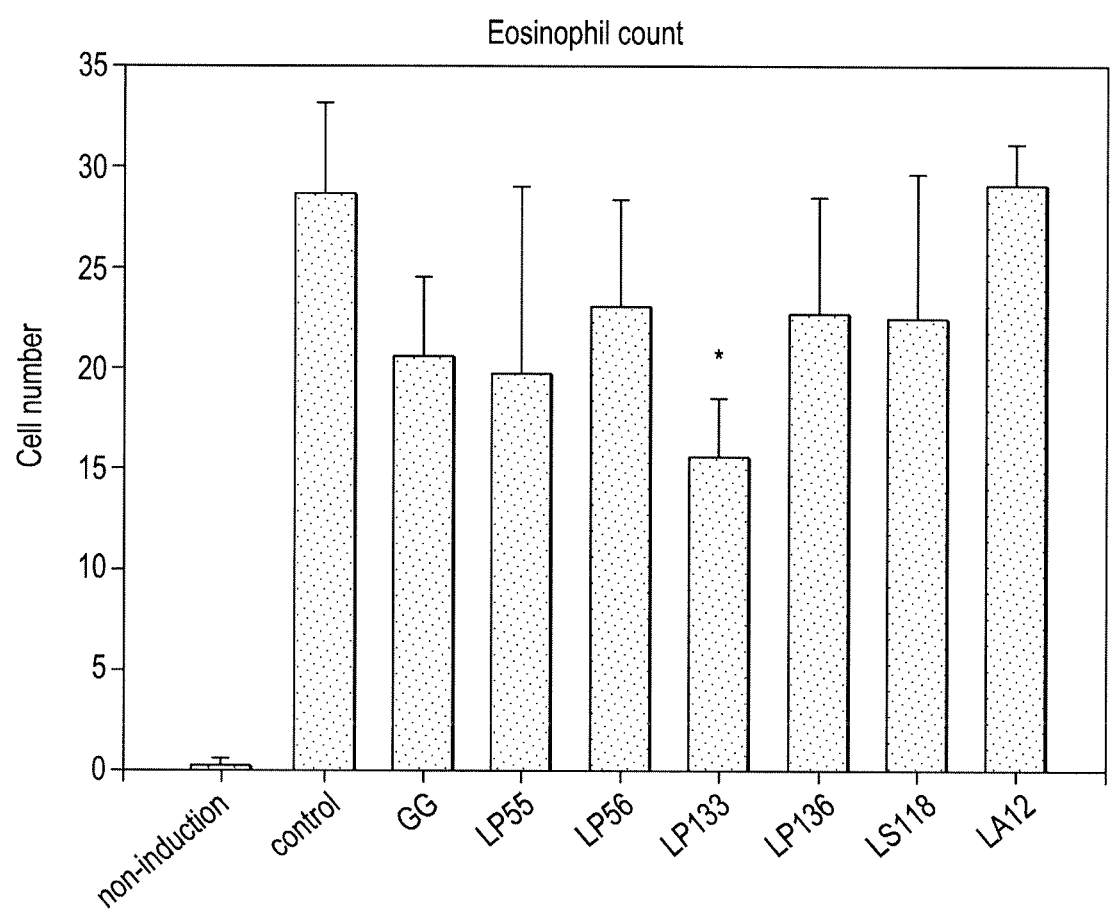
FIG. 11A shows a graph which illustrates the number of eosinophils from the skin removed from the NC/Nga mouse with atopic dermatitis which was treated with lactic acid bacteria.

FIG. 11A shows a graph which illustrates the number of eosinophils from the skin removed from the NC/Nga mouse with atopic dermatitis which was treated with lactic acid bacteria.

Figure 11B:
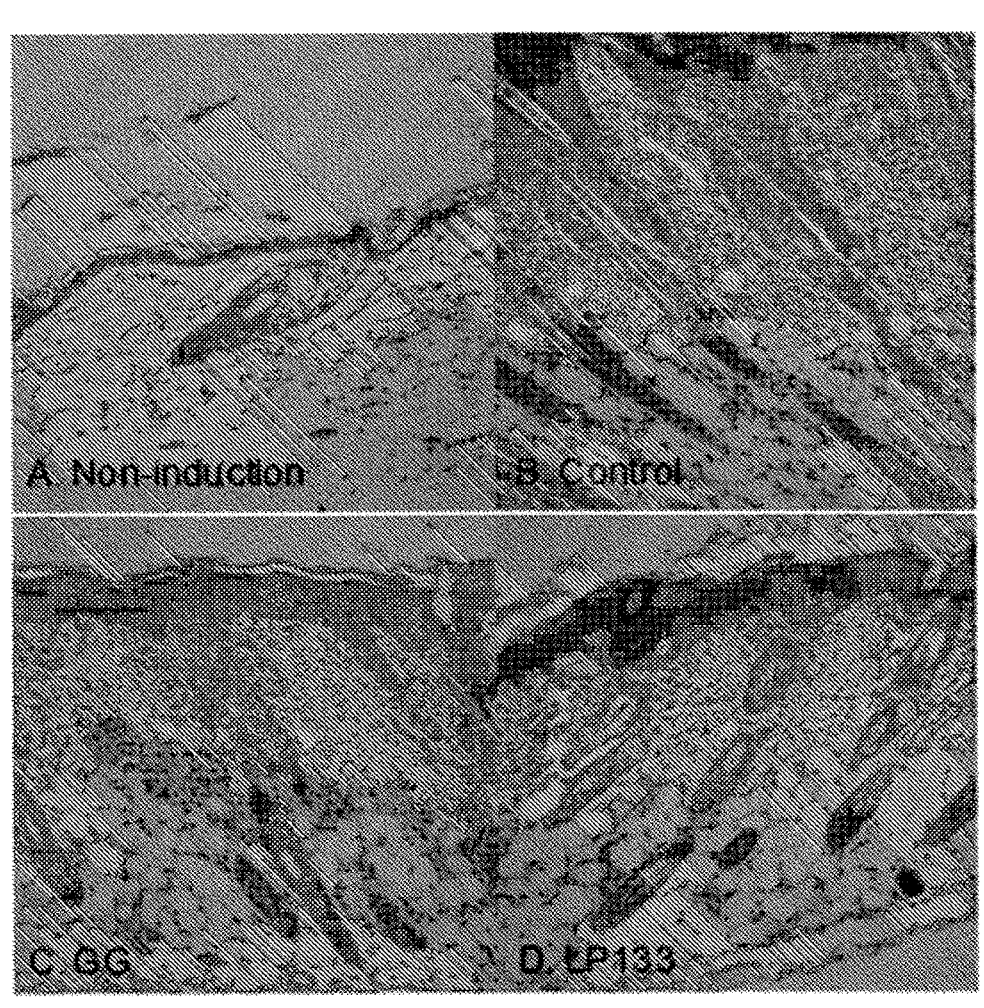
FIG. 11B shows the light microscopic photo of eosinophil infiltration within the skin removed from the NC/Nga mouse with atopic dermatitis which was treated with lactic acid bacteria.

FIG. 11B shows the light microscopic photo of eosinophil infiltration within the skin removed from the NC/Nga mouse with atopic dermatitis which was treated with lactic acid bacteria.

Figure 12A:
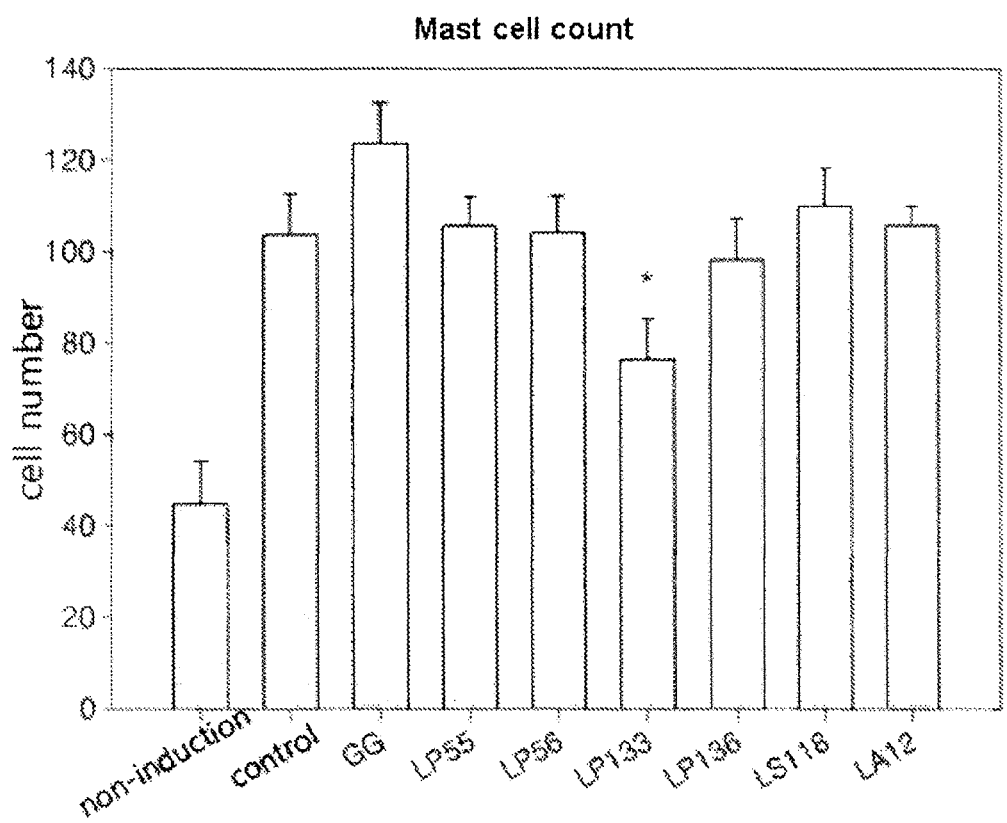
FIG. 12A shows a graph which illustrates the number of mast cells from the skin removed from the NC/Nga mouse with atopic dermatitis which was treated with lactic acid bacteria.

FIG. 12A shows a graph which illustrates the number of mast cells from the skin removed from the NC/Nga mouse with atopic dermatitis which was treated with lactic acid bacteria.

Figure 12B:
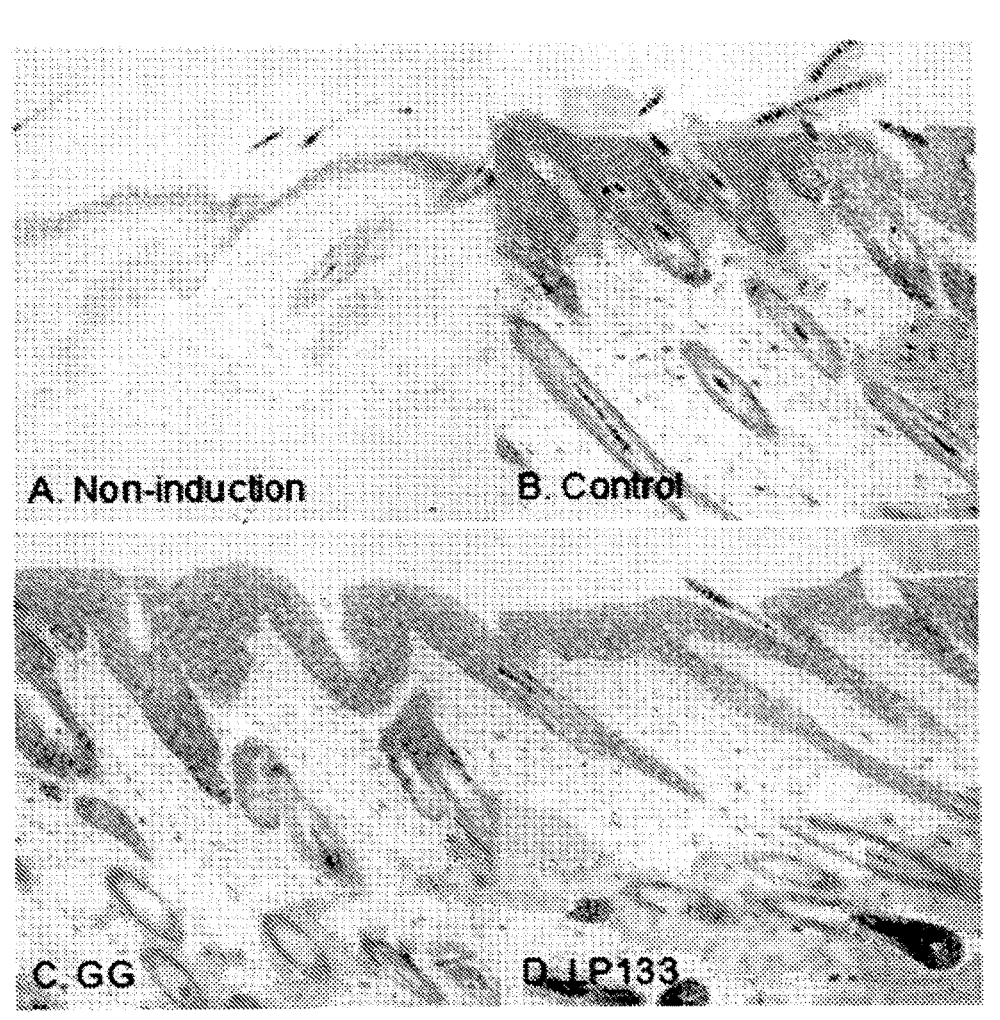
FIG. 12B shows the light microscopic photo of mast cell infiltration within the skin removed from the NC/Nga mouse with atopic dermatitis which was treated with lactic acid bacteria.

FIG. 12B shows the light microscopic photo of mast cell infiltration within the skin removed from the NC/Nga mouse with atopic dermatitis which was treated with lactic acid bacteria.

Figure 13A:
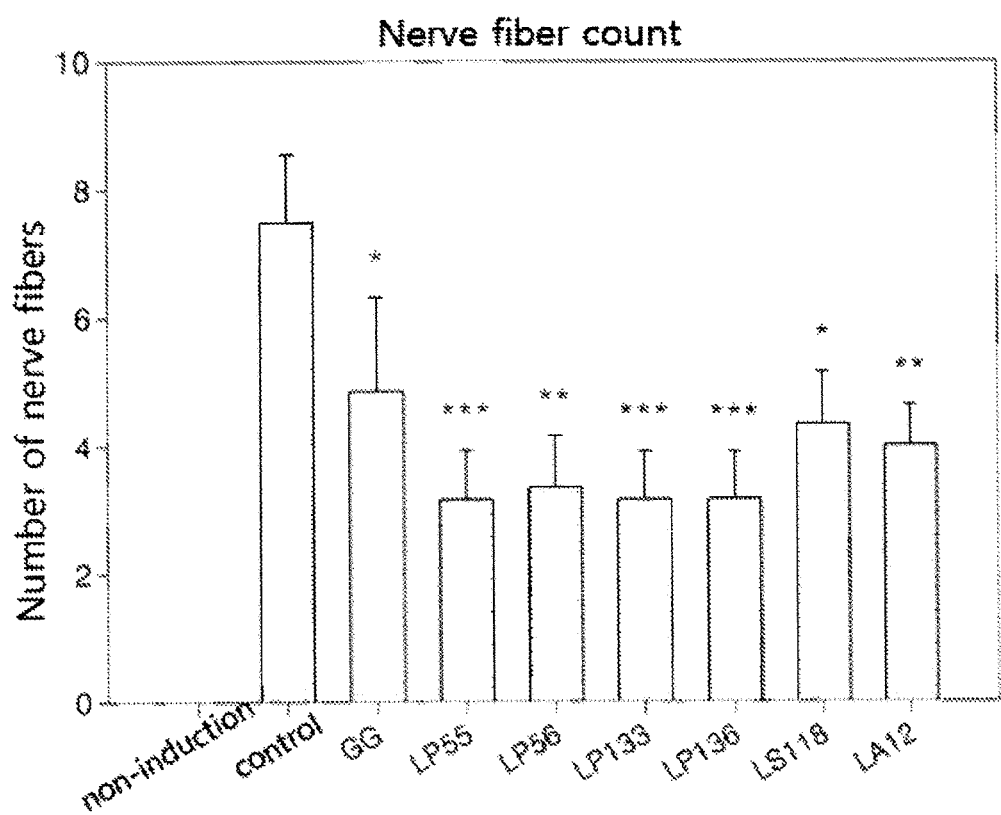
FIG. 13A shows a graph which illustrates the number of nerve fibers from the skin removed from the NC/Nga mouse with atopic dermatitis which was treated with lactic acid bacteria.

FIG. 13A shows a graph which illustrates the number of nerve fibers from the skin removed from the NC/Nga mouse with atopic dermatitis which was treated with lactic acid bacteria.

Figure 13B:
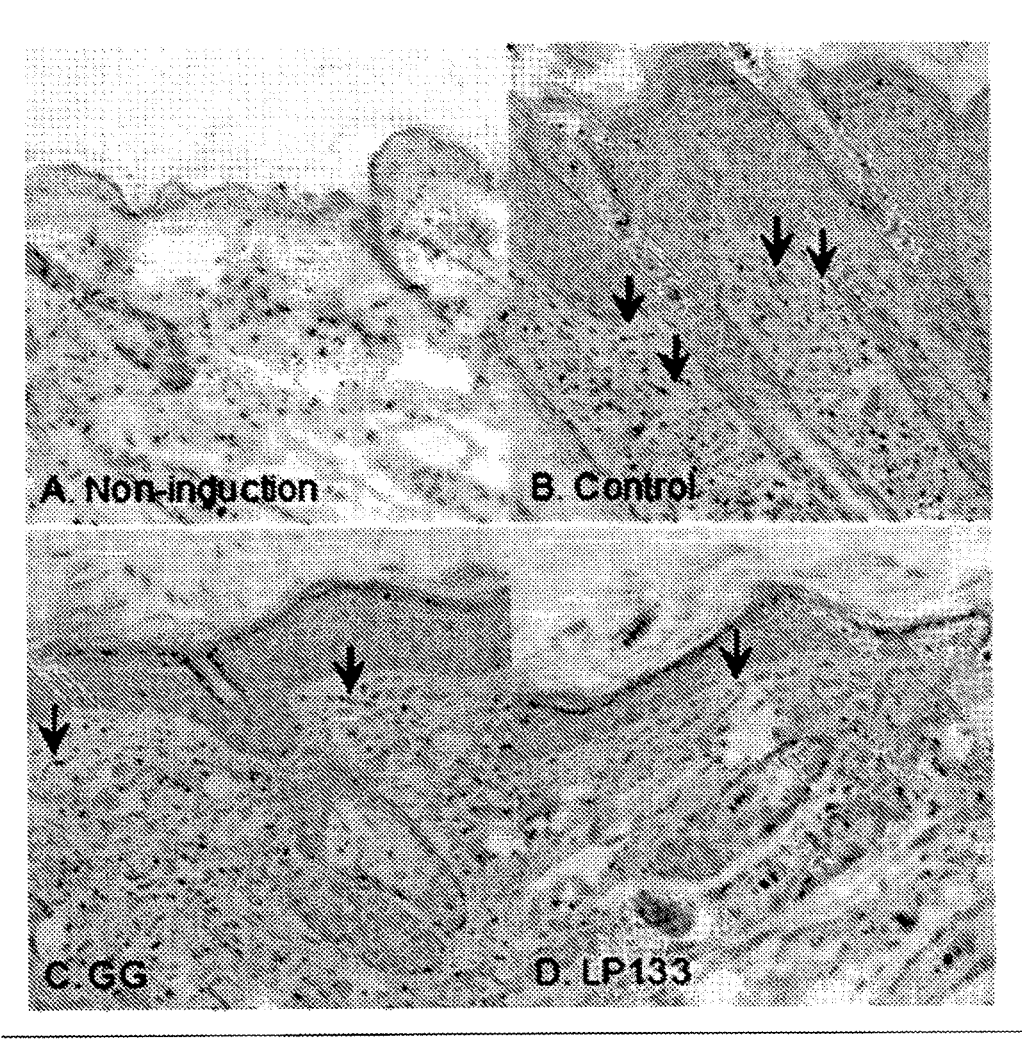
FIG. 13B shows the light microscopic photo of nerve fiber-infiltration within the skin removed from the NC/Nga mouse with atopic dermatitis which was treated with lactic acid bacteria.

FIG. 13B shows the light microscopic photo of nerve fiber-infiltration within the skin removed from the NC/Nga mouse with atopic dermatitis which was treated with lactic acid bacteria.

According to the results described above, the thickness of the skin in each experimental group composed of the NC/Nga mice induced with atopic dermatitis was approximately 100 μm.

However, the thickness of the skin in mice administered with CJLP133 was approximately 50 μm which was almost halved compared to others (FIG. 10*a*). Also, during observation of the penetration of lymphocytes and monocytes, it was found that markedly less numbers of immune cells were present in the CJLP133 administered group, whereas more immune cells were stained purple in the control and GG group (FIG. 10*b*).

Investigation of eosinophils and mast cells within the inflammatory lesion showed that the group induced with atopic dermatitis had larger numbers of eosinophils and mast cells compared with the non-induction group. However, the group that received CJLP133 had markedly less eosinophils and mast cells compared with control group and groups receiving other lactic acid bacteria (FIG. 11*a* and FIG. 12*a*). Light microscopic photos showed that there were more blue eosinophils and mast cells in control group and GG administered group. However, it also shows that there were less eosinophils and mast cells in the CJLP133 administered group (FIG. 11*b* and FIG. 12*b*).

Immunohistochemical analysis showed that the penetration of nerve fibers was not observed in the non-induction group. However, in the control group, many brown nerve fibers were found (FIG. 13*a*). In the groups administered with lactic acid bacteria, the number of nerve fibers penetrating decreased, and especially marked numbers of nerve fibers were decreased in CJLP55, CJLP133, CJLP136 administered groups (FIG. 13*b*).

Investigation of the composition of axillary lymph node and splenocyte Axillary lymph node (ALN) is an important immune organ which plays a major role in the animal model of chronic atopic dermatitis. There are reports from some patients with serious chronic atopic dermatitis, that the size of their axillary lymph node was increased. In the NC/Nga mouse which is an animal model of atopic dermatitis induced by dust mites, axillary lymph node has been the target lymph node for investigation in many researches. Therefore, in the present study, axillary lymph node and spleen which is the main immune organ was removed in order to observe the change in size and composition of the cells.

Five weeks after the induction of atopic dermatitis, the mouse was culled to remove the axillary lymph node and the spleen to compare the size. Then red blood cells were removed from these organs to obtain single cell suspension. $1 \times 10^6$ cells in suspension was distributed in each FACS tubes and were stained with anti-Thy1.2-FITC, anti-CD19-FITC, anti-F4/80-FITC, anti-CD11c-FITC for FACS analysis in order to study the composition of T and B lymphocytes. The results are shown in FIG. 14 to FIG. 17.

FIG. 14 shows the light microscopic photo of axillary lymph node (A) and spleen (B) removed from the NC/Nga mouse with atopic dermatitis which was treated with lactic acid bacteria.

FIG. 15 shows a graph illustrating the total number of cells counted from the axillary lymph node (A) and spleen (B) removed from the NC/Nga mouse with atopic dermatitis which was treated with lactic acid bacteria.

FIG. 16 shows a graph illustrating the total number of T cells counted from the axillary lymph node (A) and spleen (B) removed from the NC/Nga mouse with atopic dermatitis which was treated with lactic acid bacteria.

FIG. 17 shows a graph illustrating the total number of B cells counted from the axillary lymph node (A) and spleen (B) removed from the NC/Nga mouse with atopic dermatitis which was treated with lactic acid bacteria.

Figure 14A:
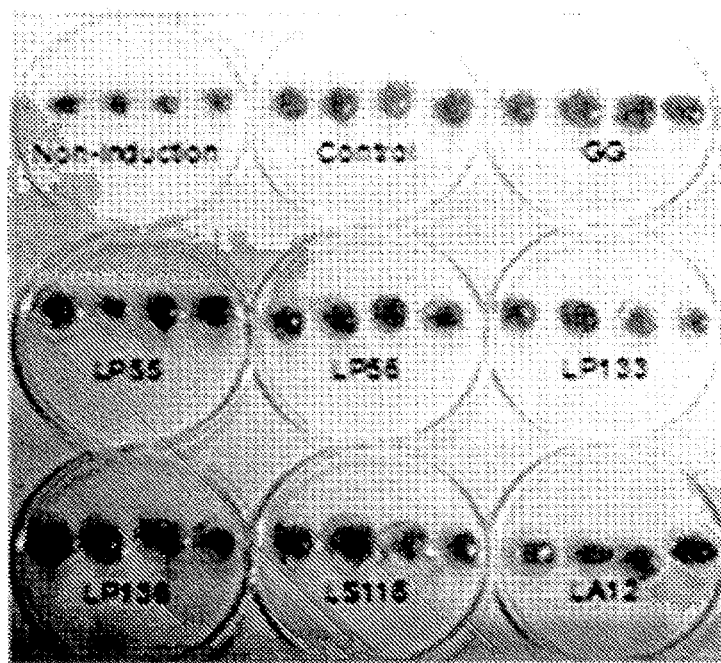
FIG. 14A shows the light microscopic photo of axillary lymphacytic gland removed from the NC/Nga mouse with atopic dermatitis which was treated with lactic acid bacteria.
Figure 14B:
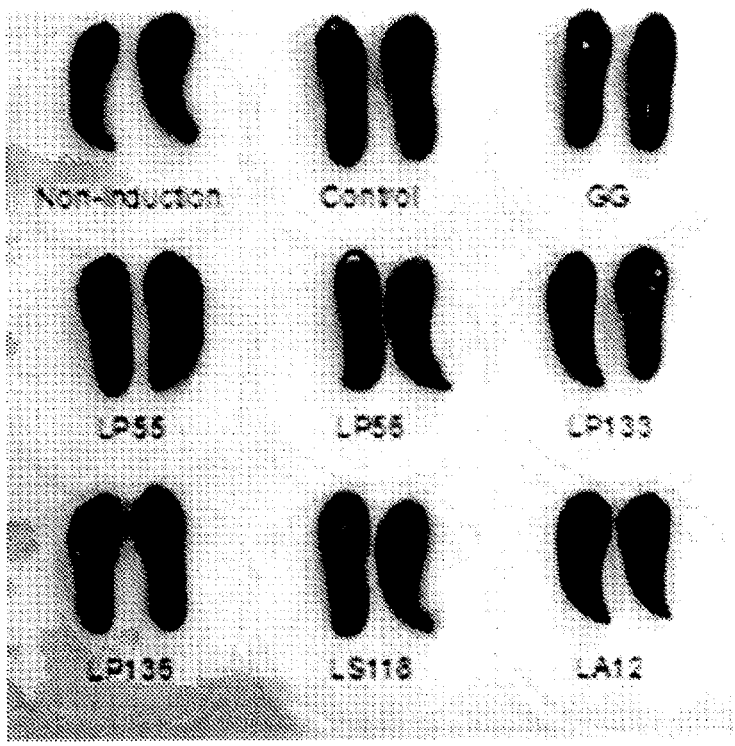
FIG. 14B shows the light microscopic photo of spleen removed from the NC/Nga mouse with atopic dermatitis which was treated with lactic acid bacteria.
Figure 15A:
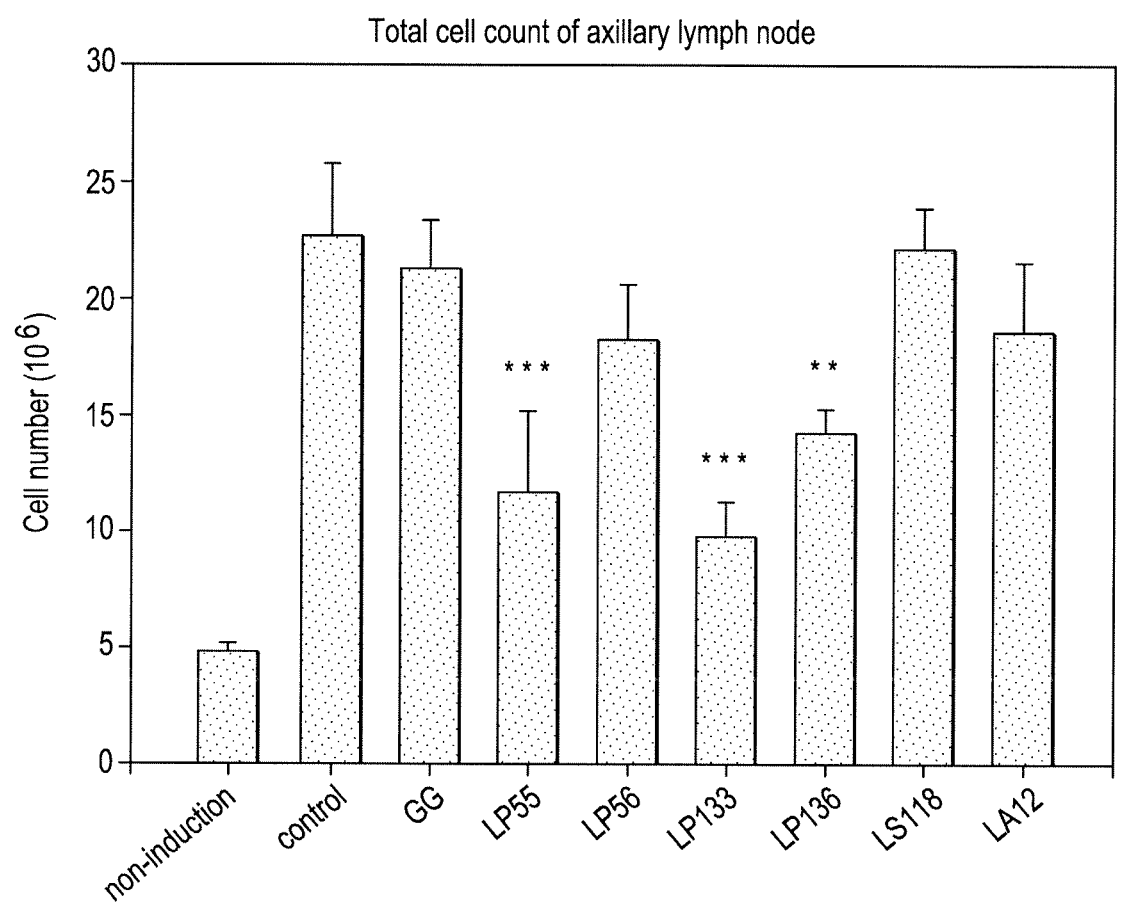
FIG. 15A shows a graph illustrating the total number of cells counted from the axillary lymphacytic gland removed from the NC/Nga mouse with atopic dermatitis which was treated with lactic acid bacteria.
Figure 15B:
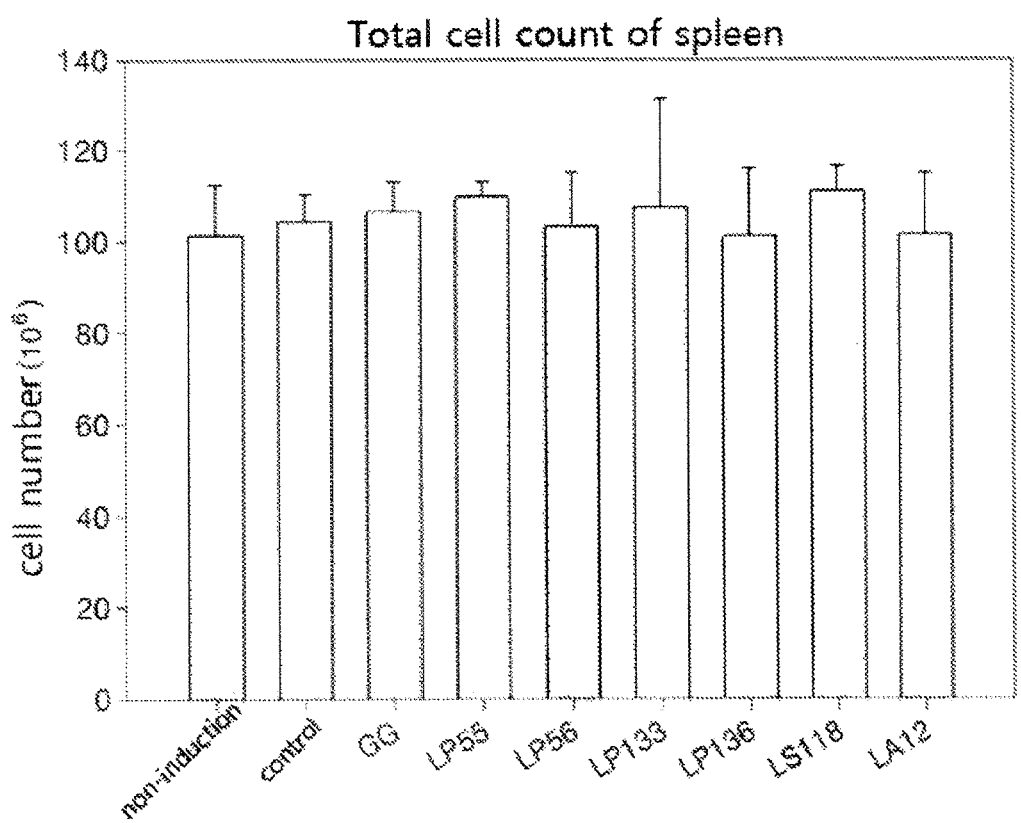
FIG. 15B shows a graph illustrating the total number of cells counted from the spleen removed from the NC/Nga mouse with atopic dermatitis which was treated with lactic acid bacteria.

According to the results above, the size of axillary lymph node had increased in the control group induced with atopic dermatitis, and the size was similar in GG administered group. However, the size of axillary lymph node of the group administered with CJLP55, CJLP56, CJLP133, CJLP136, CJLS118 was smaller than the control group (FIG. 14A). The spleen did not show much difference in size comparing the groups (FIG. 14B). The number of cells isolated from the axillary lymph node was 4.5 times larger in control group compared with non-induction group. However, the number of cells was significantly smaller in the group administered with CJLP55, CJLP133, CJLP136 compared with the control group (FIG. 15A). The number of cells in the spleen did not show much difference among the different groups (FIG. 15B).

Figure 16A:
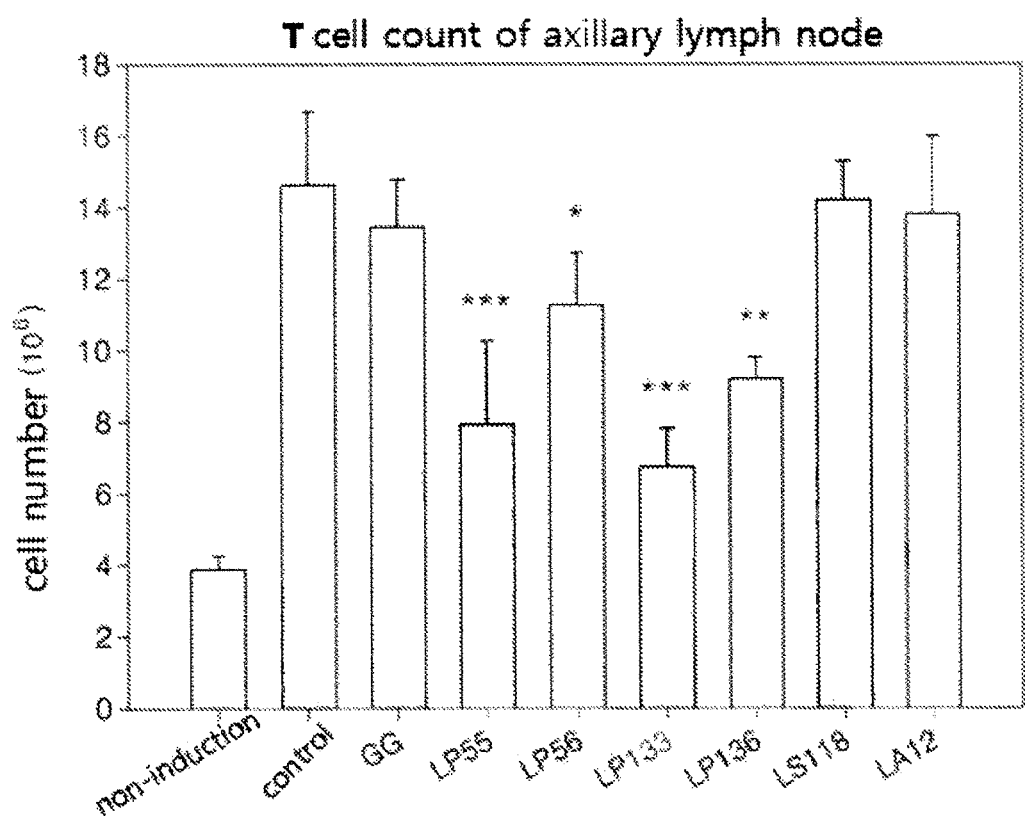
FIG. 16A shows a graph illustrating the total number of T cells counted from the axillary lymphacytic gland removed from the NC/Nga mouse with atopic dermatitis which was treated with lactic acid bacteria.
Figure 16B:
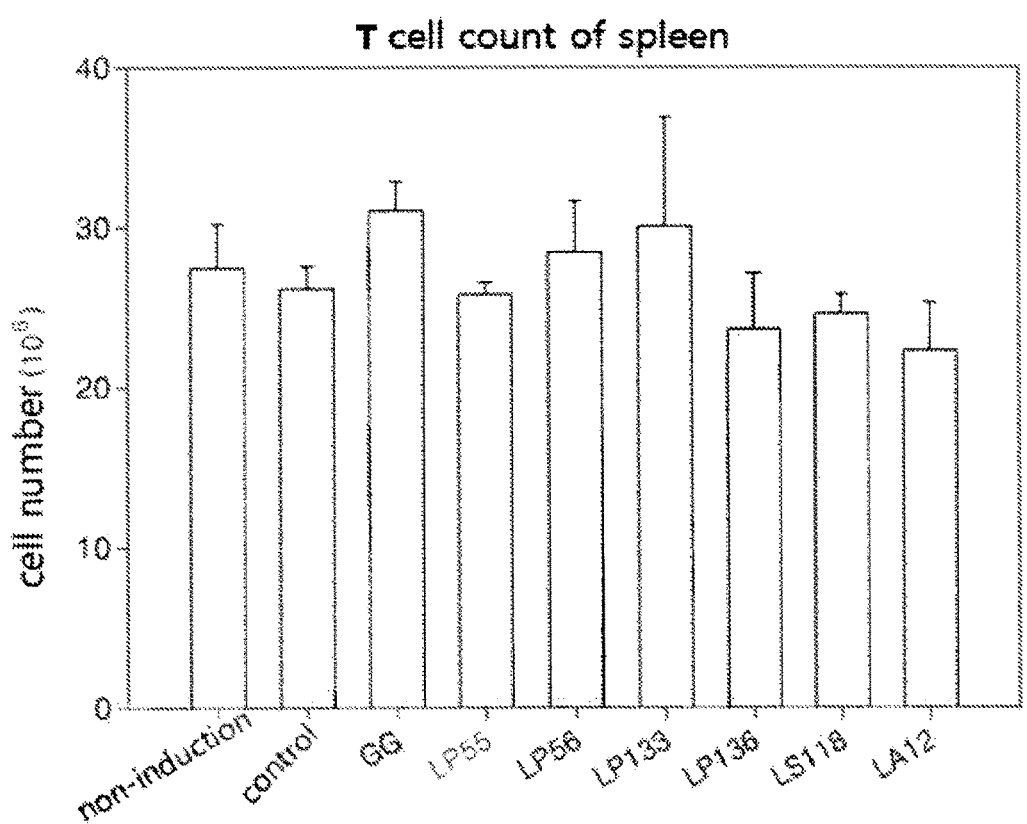
FIG. 16B shows a graph illustrating the total number of T cells counted from the spleen removed from the NC/Nga mouse with atopic dermatitis which was treated with lactic acid bacteria.
Figure 17A:
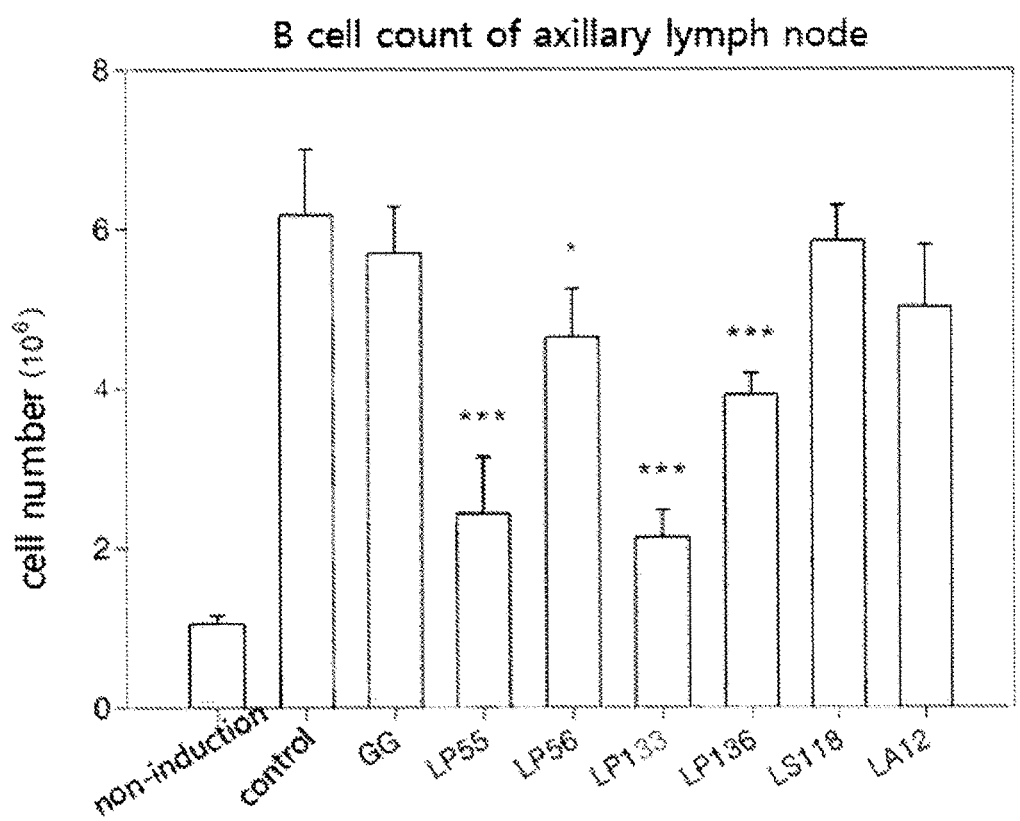
FIG. 17A shows a graph illustrating the total number of B cells counted from the axillary lymphacytic gland removed from the NC/Nga mouse with atopic dermatitis which was treated with lactic acid bacteria.
Figure 17B:
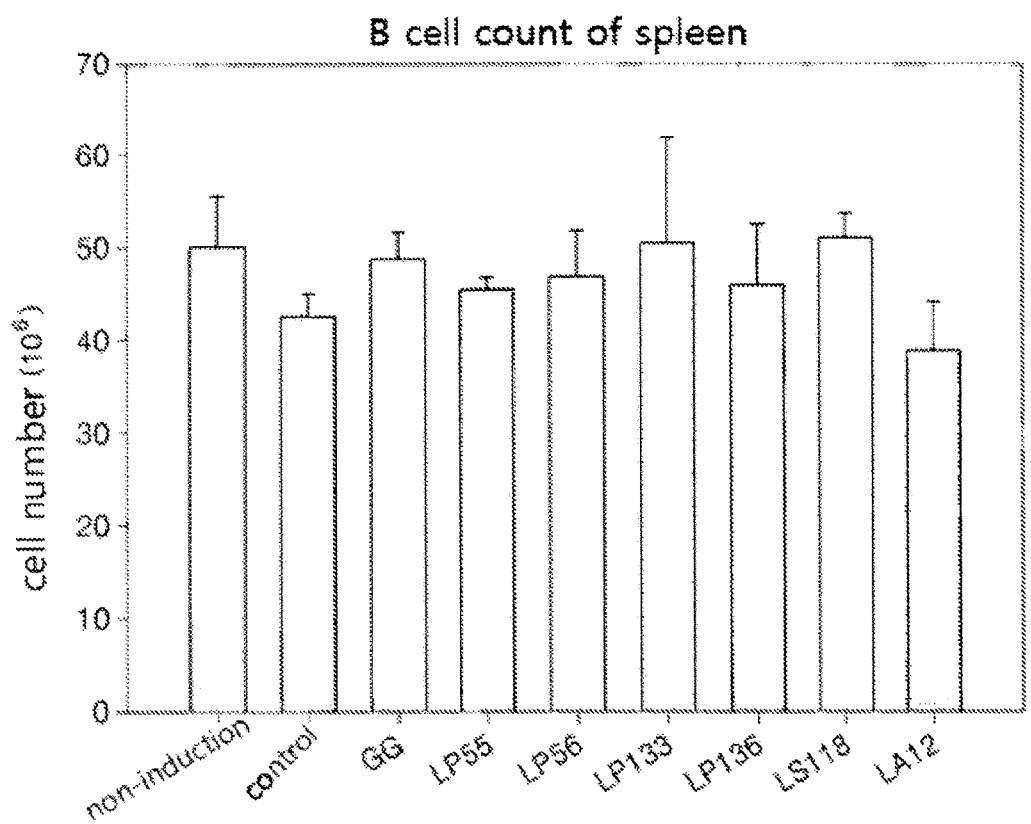
FIG. 17B shows a graph illustrating the total number of B cells counted from the spleen removed from the NC/Nga mouse with atopic dermatitis which was treated with lactic acid bacteria.

Investigation of the T and B lymphocytes was performed in the axillary lymph node and spleen by staining and FACS analysis. The number of T and B lymphocytes from the axillary lymph node increased five times in the control group induced with atopic dermatitis. However, the number of cells in all the groups administered with CJLP55, CJLP56, CJLP133, CJLP136 was significantly decreased compared with control group. Especially, the number of cells was remarkably decreased in the CJLP133 group compared with other lactic acid administered groups (FIG. 16A and FIG. 17A). The number of T and B lymphocytes did not show much difference (FIG. 16B and FIG. 17B).

5) Ability of cytokine production of axillary lymph node cells and splenocytes IL-12 which is produced mainly by macrophages induces the differentiation of Th0 lymphocyte into Th1 lymphocyte. IFN-γ which is produced by Th1 lymphocyte not only activates macrophages but also suppresses the differentiation into Th2 cells and its activity. Therefore, the changes in concentrations of IL-12 and IFN-γ produced were measured.

The single cell suspension was obtained from the previously mentioned experiment 4) Investigation of the composition of axillary lymph node and splenocyte. The suspension was added to each of the wells of the 24-well plate in a concentration of $5 \times 10^6$ cells per plate, and 10 μg/ml of dust mite (*Dermatophagoides farinae* body, Dfb) extraction was added as well. The plate was kept at 37° C. for 48 hours for culture, and then the concentrations of IFN-γ and IL-12 was measured using ELISA. The results are illustrated in FIG. 18 and FIG. 19.

Figure 18A:
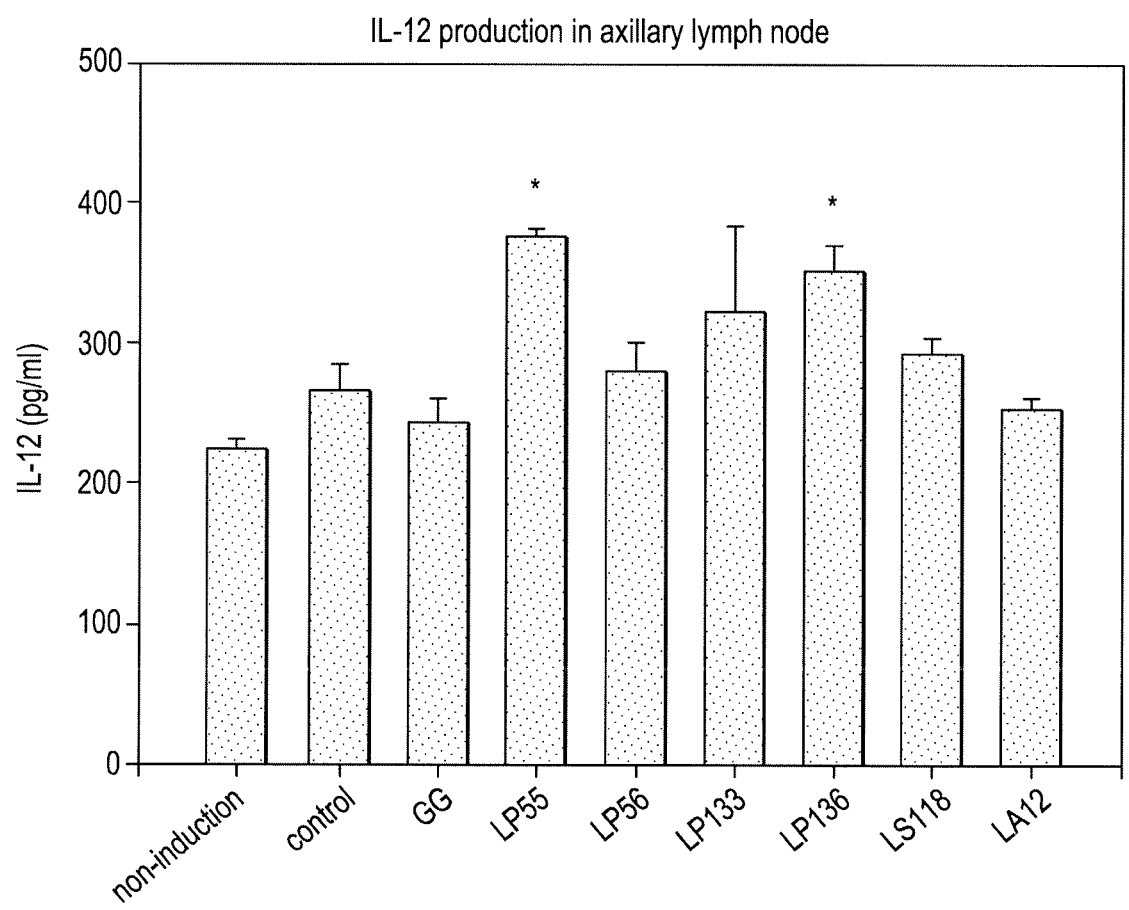
FIG. 18A shows a graph illustrating IL-12 concentrations using ELISA from single cell suspension of axillary lymph node removed from the NC/Nga mouse with atopic dermatitis which was treated with lactic acid bacteria, after culturing with dust mite extract.
Figure 18B:
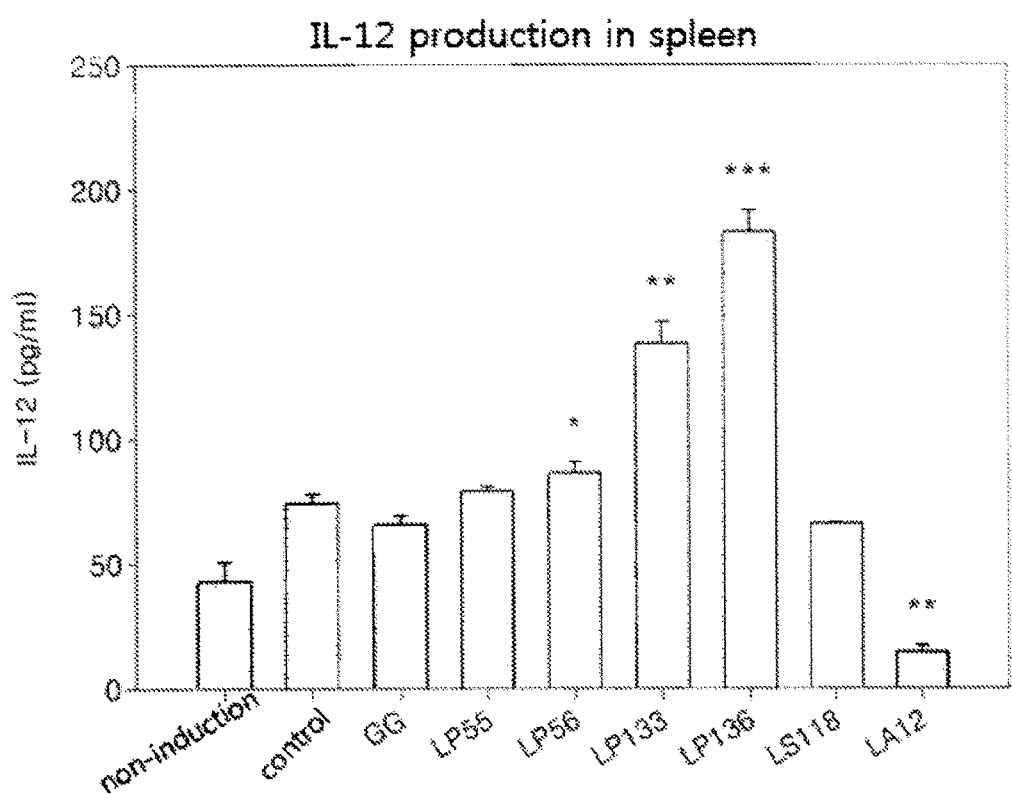
FIG. 18B shows a graph illustrating IL-12 concentrations using ELISA from single cell suspension of spleen removed from the NC/Nga mouse with atopic dermatitis which was treated with lactic acid bacteria, after culturing with dust mite extract.

FIG. 18 shows a graph illustrating IL-12 concentrations using ELISA from single cell suspension of axillary lymph node (A) and spleen (B) removed from the NC/Nga mouse with atopic dermatitis which was treated with lactic acid bacteria, after culturing with dust mite extract.

Figure 19A:
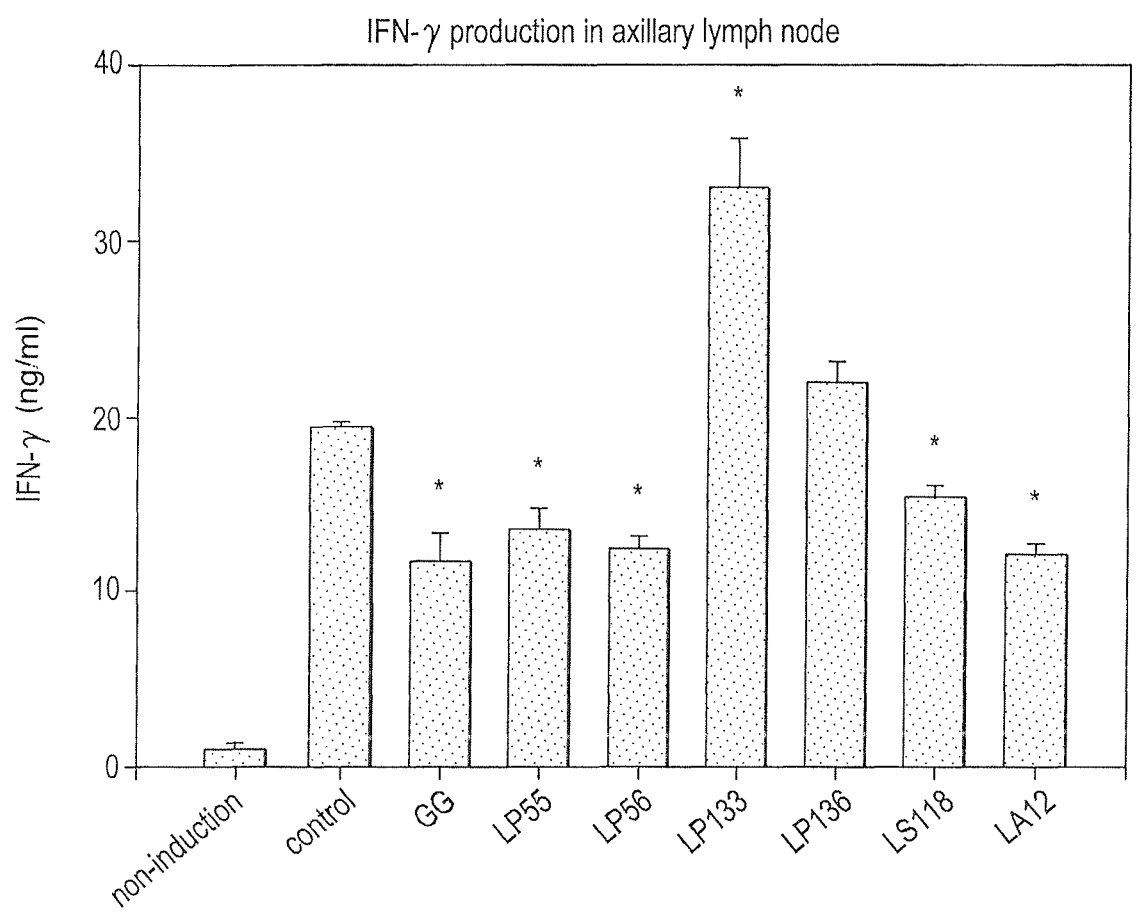
FIG. 19A shows a graph illustrating IFN-γ concentrations using ELISA from single cell suspension of axillary lymph node removed from the NC/Nga mouse with atopic dermatitis which was treated with lactic acid bacteria, after culturing with dust mite extract.
Figure 19B:
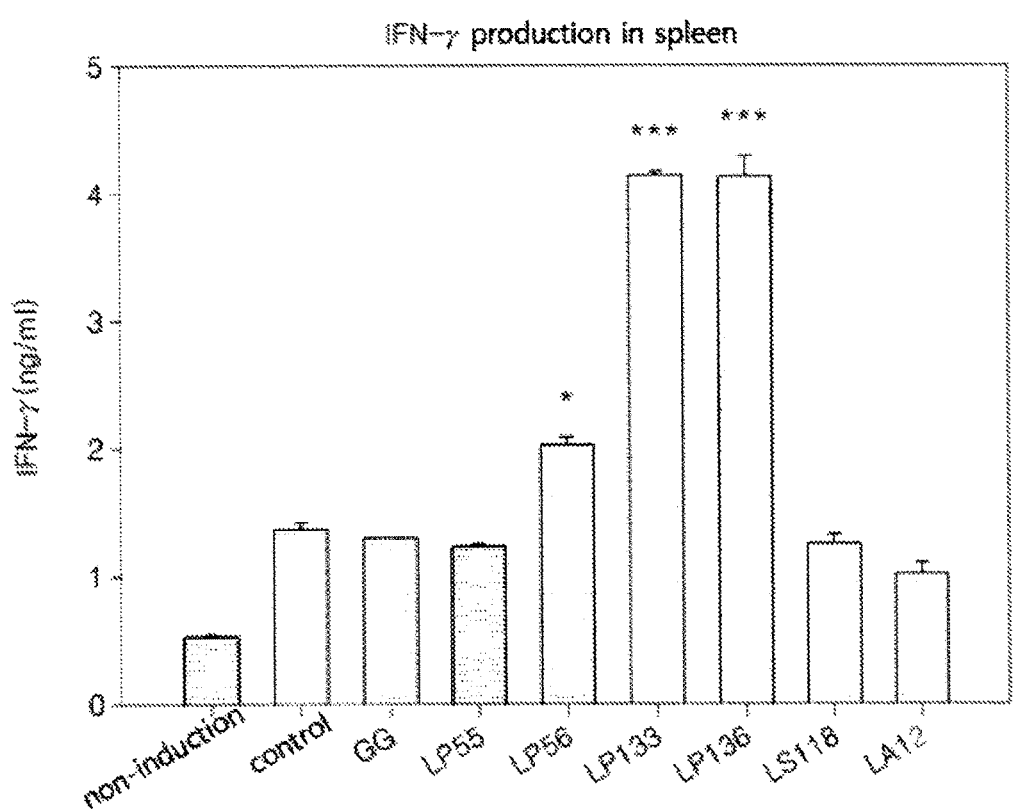
FIG. 19B shows a graph illustrating IFN-γ concentrations using ELISA from single cell suspension of spleen removed from the NC/Nga mouse with atopic dermatitis which was treated with lactic acid bacteria, after culturing with dust mite extract.

FIG. 19 shows a graph illustrating IFN-γ concentrations using ELISA from single cell suspension of axillary lymph node (A) and spleen (B) removed from the NC/Nga mouse with atopic dermatitis which was treated with lactic acid bacteria, after culturing with dust mite extract.

According to the results, the concentrations of IL-12 (FIG. 18) and IFN-γ (FIG. 19) were remarkably increased in the group receiving CJLP133 compared with control group. Also, the concentration of these cytokines were remarkably larger compared with other groups administered with other known lactic acid bacteria.

All the groups administered with CJLP55, CJLP56, CJLP133, CJLP136 showed an improvement of atopic dermatitis symptoms, summarising the results from the experiment 1) to 5) as described above. Especially, CJLP133 was even more effective for atopic dermatitis compared with other known lactic bacteria, supported by its cellular and molecular effects on the animals, such as the size of axillary lymph node, number of cells in the axillary lymph node, penetration of immune cells or nerve cells into inflammatory skin lesions, and the balance of Th1/Th2 cytokines.

EXAMPLE 9: MANUFACTURING PROBIOTICS INCLUDING *LACTOBACILLUS PLANTARUM* CJLP133

*Lactobacillus plantarum* CJLP133 identified as described in Example 1 was mass produced and lyophilised to be manufactured into probiotics in order to be used as medicine, food, feedstuff, feed additives, or material for cosmetics.

For mass production, the bacteria was cultured in MRS liquid medium (Difco) added with 25% NaOH to reach pH 6.0 for 18 hours at 37° C. Then the bacteria was obtained by centrifugation. The bacteria was then frozen at −40° C. using 5% dextrin and 10% skimmed milk as a protector, and the dried bacteria was ground using a mixer to be in a power form. The powdered bacteria was stored and packed in an aluminium pouch bag mixed with an appropriate amount of diluting agent such as glucose, lactose, skimmed milk.

The manufactured probiotics can be used as feed probiotics by mixing with feed material such as grain powder; as medicine or health food in a form of tablets or capsules mixed with carriers or additives; as cosmetics after being mixed with other cosmetic material. The probiotics could be used in various industries such as medicine, food, feedstuff, cosmetics according to the conventional methods in the art.

What is claims is:

1. A method for improving a microbial environment in a gastrointestinal tract of a subject, comprising:
    administering a composition comprising *Lactobacillus plantarum* CJLP133 strain KCTC 11403BP to the subject in need thereof.

2. The method of claim 1, wherein the composition is selected from the group consisting of pharmaceuticals, food, animal feed, feed additives and cosmetics.

3. The method of claim 1, wherein the subject is a human.

4. The method of claim 1, wherein the composition is administered orally.

* * * * *